United States Patent
Morris

(10) Patent No.: US 12,171,443 B1
(45) Date of Patent: Dec. 24, 2024

(54) MAGNETICALLY CONTROLLED FLOW GENERATION

(71) Applicant: Pulse Therapeutics, Inc., St. Louis, MO (US)

(72) Inventor: Sean C. Morris, Wildwood, MO (US)

(73) Assignee: Pulse Therapeutics, Inc., St. Louis, MO (US)

( * ) Notice: Subject to any disclaimer, the term of this patent is extended or adjusted under 35 U.S.C. 154(b) by 0 days.

(21) Appl. No.: 17/653,939

(22) Filed: Mar. 8, 2022

Related U.S. Application Data

(60) Provisional application No. 63/200,476, filed on Mar. 9, 2021.

(51) Int. Cl.
 *A61B 17/22* (2006.01)
 *A61B 17/00* (2006.01)
 *A61K 41/00* (2020.01)

(52) U.S. Cl.
 CPC .......... *A61B 17/22* (2013.01); *A61K 41/0028* (2013.01); *A61B 2017/00867* (2013.01); *A61B 2017/00876* (2013.01); *A61B 2017/22078* (2013.01); *A61B 2017/22084* (2013.01)

(58) Field of Classification Search
 CPC .......... A61B 17/22; A61B 2017/00867; A61B 2017/22078; A61B 2017/22084
 See application file for complete search history.

(56) References Cited

U.S. PATENT DOCUMENTS

| | | | |
|---|---|---|---|
| 3,474,777 A | 10/1969 | Figge et al. | |
| 4,141,687 A | 2/1979 | Forrest et al. | |
| 4,359,453 A | 11/1982 | Gordon | |
| 4,916,070 A | 4/1990 | Matsueda et al. | |
| 5,078,140 A | 1/1992 | Kwoh | |
| 5,110,727 A | 5/1992 | Oberhardt | |
| 5,401,253 A | 3/1995 | Reynolds | |
| 5,543,158 A | 8/1996 | Gref et al. | |
| 5,654,864 A | 8/1997 | Ritter et al. | |

(Continued)

FOREIGN PATENT DOCUMENTS

| | | |
|---|---|---|
| DE | 2450098 A1 | 4/1976 |
| DE | 102005030986 | 1/2007 |

(Continued)

OTHER PUBLICATIONS

Califf, Robert M. et al., "Hemorrhagic Complications Associated With The Use Of Intravenous Tissue Plasminogen Activator In Treatment Of Acute Myocardial Infarction," The American Journal of Medicine, Sep. 1988, pp. 353-359, vol. 85, Issue 3.

(Continued)

*Primary Examiner* — Jocelin C Tanner
(74) *Attorney, Agent, or Firm* — Goodwin Procter LLP

(57) ABSTRACT

This disclosure generally relates to systems and methods for facilitating flow within vasculature or other body lumens, channels or passages involving a magnetic field generated by an external magnetic control system and/or facilitating clearance of obstructions (e.g., clots, fluid obstructions) within in-dwelling devices (e.g., shunts, drains, conduits, ports, catheters) involving magnetic particles (e.g., nanoparticles, microparticles) controlled by an external magnetic control system (e.g., one or more rotating permanent magnets or an electromagnetic control system).

14 Claims, 9 Drawing Sheets

(56) References Cited

U.S. PATENT DOCUMENTS

| | | |
|---|---|---|
| 5,665,277 A | 9/1997 | Johnson et al. |
| 5,916,539 A | 6/1999 | Pilgrimm |
| 5,931,818 A | 8/1999 | Werp et al. |
| 6,014,580 A | 1/2000 | Blume et al. |
| 6,015,414 A | 1/2000 | Werp et al. |
| 6,128,174 A | 10/2000 | Ritter et al. |
| 6,148,823 A | 11/2000 | Hastings |
| 6,152,933 A | 11/2000 | Werp et al. |
| 6,157,853 A | 12/2000 | Blume et al. |
| 6,212,419 B1 | 4/2001 | Blume et al. |
| 6,231,496 B1 | 5/2001 | Wilk et al. |
| 6,241,671 B1 | 6/2001 | Ritter et al. |
| 6,292,678 B1 | 9/2001 | Hall et al. |
| 6,296,604 B1 | 10/2001 | Garibaldi et al. |
| 6,296,639 B1 * | 10/2001 | Truckai ............... A61B 18/082 606/41 |
| 6,304,768 B1 | 10/2001 | Blume et al. |
| 6,311,082 B1 | 10/2001 | Creighton, IV et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,358,244 B1 | 3/2002 | Newman et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,475,223 B1 | 11/2002 | Werp et al. |
| 6,482,436 B1 | 11/2002 | Volkonsky et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,529,761 B2 | 3/2003 | Creighton, IV et al. |
| 6,537,196 B1 | 3/2003 | Creighton, IV et al. |
| 6,541,039 B1 | 4/2003 | Lesniak et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,638,494 B1 | 10/2003 | Pilgrimm |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,740,103 B2 | 5/2004 | Hall et al. |
| 6,755,816 B2 | 6/2004 | Ritter et al. |
| 6,786,219 B2 | 9/2004 | Garibaldi et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,979,466 B2 | 12/2005 | Lesniak et al. |
| 6,980,843 B2 | 12/2005 | Eng et al. |
| 7,008,418 B2 | 3/2006 | Hall et al. |
| 7,010,338 B2 | 3/2006 | Ritter et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| 7,052,777 B2 | 3/2006 | Brotzman, Jr. et al. |
| 7,066,924 B1 | 6/2006 | Garibaldi et al. |
| 7,074,175 B2 | 7/2006 | Handy et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al. |
| 7,248,914 B2 | 7/2007 | Hastings et al. |
| 7,249,604 B1 | 7/2007 | Mohanraj |
| 7,264,584 B2 | 9/2007 | Ritter et al. |
| 7,276,044 B2 | 10/2007 | Ferry et al. |
| 7,286,034 B2 | 10/2007 | Creighton |
| 7,305,263 B2 | 12/2007 | Creighton, IV |
| 7,313,429 B2 | 12/2007 | Creighton, IV et al. |
| 7,329,638 B2 | 2/2008 | Yang et al. |
| 7,341,063 B2 | 3/2008 | Garbibaldi et al. |
| 7,346,379 B2 | 3/2008 | Eng et al. |
| 7,389,778 B2 | 6/2008 | Sabo et al. |
| 7,416,335 B2 | 8/2008 | Munger |
| 7,452,551 B1 | 11/2008 | Unger et al. |
| 7,459,145 B2 | 12/2008 | Bao et al. |
| 7,495,537 B2 | 2/2009 | Tunay |
| 7,502,640 B2 | 3/2009 | Conolly et al. |
| 7,505,615 B2 | 3/2009 | Viswanathan |
| 7,516,416 B2 | 4/2009 | Viswanathan et al. |
| 7,524,630 B2 | 4/2009 | Tan et al. |
| 7,537,570 B2 | 5/2009 | Kastelein |
| 7,540,288 B2 | 6/2009 | Viswanathan et al. |
| 7,540,866 B2 | 6/2009 | Viswanathan et al. |
| 7,543,239 B2 | 6/2009 | Viswanathan et al. |
| 7,555,331 B2 | 6/2009 | Viswanathan |
| 7,567,233 B2 | 7/2009 | Garibaldi et al. |
| 7,603,905 B2 | 10/2009 | Creighton, IV |
| 7,623,736 B2 | 11/2009 | Viswanathan |
| 7,625,382 B2 | 12/2009 | Werp et al. |
| 7,627,361 B2 | 12/2009 | Viswanathan |
| 7,630,752 B2 | 12/2009 | Viswanathan |
| 7,635,342 B2 | 12/2009 | Ferry et al. |
| 7,657,075 B2 | 2/2010 | Viswanathan |
| 7,662,126 B2 | 2/2010 | Creighton, IV |
| 7,690,619 B2 | 4/2010 | Wolfersberger |
| 7,708,696 B2 | 5/2010 | Ritter et al. |
| 7,713,239 B2 | 5/2010 | Uber, III et al. |
| 7,742,803 B2 | 6/2010 | Viswanathan et al. |
| 7,747,960 B2 | 6/2010 | Garibaldi et al. |
| 7,751,867 B2 | 7/2010 | Viswanathan |
| 7,756,308 B2 | 7/2010 | Viswanathan |
| 7,757,694 B2 | 7/2010 | Ritter et al. |
| 7,761,133 B2 | 7/2010 | Viswanathan et al. |
| 7,766,856 B2 | 8/2010 | Ferry et al. |
| 7,769,428 B2 | 8/2010 | Viswanathan et al. |
| 7,769,444 B2 | 8/2010 | Pappone |
| 7,771,415 B2 | 8/2010 | Ritter et al. |
| 7,771,437 B2 | 8/2010 | Hogg et al. |
| 7,772,950 B2 | 8/2010 | Tunay |
| 7,774,046 B2 | 8/2010 | Werp et al. |
| 7,815,580 B2 | 10/2010 | Viswanathan |
| 7,818,076 B2 | 10/2010 | Viswanathan |
| 7,831,294 B2 | 11/2010 | Viswanathan |
| 7,846,201 B2 | 12/2010 | Chorny et al. |
| 7,853,306 B2 | 12/2010 | Viswanathan et al. |
| 7,892,233 B2 | 2/2011 | Hall et al. |
| 7,961,924 B2 | 6/2011 | Viswanathan |
| 7,961,926 B2 | 6/2011 | Viswanathan |
| 7,966,059 B2 | 6/2011 | Creighton, IV et al. |
| 7,968,117 B1 | 6/2011 | Morrisson et al. |
| 7,983,733 B2 | 7/2011 | Viswanathan |
| 7,998,020 B2 | 8/2011 | Kidd et al. |
| 8,024,024 B2 | 9/2011 | Viswanathan et al. |
| 8,060,184 B2 | 11/2011 | Hastings et al. |
| 8,088,129 B2 | 1/2012 | Werp et al. |
| 8,092,450 B2 | 1/2012 | Davies et al. |
| 8,114,032 B2 | 2/2012 | Ferry et al. |
| 8,135,185 B2 | 3/2012 | Blume et al. |
| 8,162,920 B2 | 4/2012 | Ritter et al. |
| 8,192,374 B2 | 6/2012 | Viswanathan |
| 8,196,590 B2 | 6/2012 | Sabo et al. |
| 8,246,975 B2 | 8/2012 | Eguchi et al. |
| 8,251,885 B2 | 8/2012 | Ueda et al. |
| 8,278,274 B2 | 10/2012 | Bussat et al. |
| 8,293,213 B2 | 10/2012 | Schwartz et al. |
| 8,308,628 B2 | 11/2012 | Creighton |
| 8,313,422 B2 | 11/2012 | Creighton |
| 8,369,934 B2 | 2/2013 | Viswanathan |
| 8,500,619 B2 | 8/2013 | Brown et al. |
| 8,529,428 B2 | 9/2013 | Creighton |
| 8,562,505 B2 | 10/2013 | Levy et al. |
| 8,568,286 B2 | 10/2013 | Sih et al. |
| 8,579,787 B2 | 11/2013 | Shapiro et al. |
| 8,689,800 B2 | 4/2014 | Lin et al. |

(56) References Cited

U.S. PATENT DOCUMENTS

| | | |
|---|---|---|
| 8,691,261 B2 | 4/2014 | Eguchi et al. |
| 8,715,150 B2 | 5/2014 | Creighton |
| 8,888,674 B2 | 11/2014 | Shapiro et al. |
| 8,897,856 B2 | 11/2014 | Gaitas |
| 8,926,491 B2 | 1/2015 | Creighton |
| 8,968,699 B2 | 3/2015 | Jin et al. |
| 9,028,829 B2 | 5/2015 | Levy et al. |
| 9,108,035 B2 | 8/2015 | Shapiro et al. |
| 9,138,293 B1 | 9/2015 | Weisman |
| 9,339,664 B2 | 5/2016 | Creighton |
| 9,345,498 B2 | 5/2016 | Creighton |
| 9,883,878 B2 | 2/2018 | Creighton et al. |
| 10,029,008 B2 | 7/2018 | Creighton |
| 10,159,734 B2 | 12/2018 | Creighton |
| 10,646,241 B2 | 5/2020 | Creighton et al. |
| 10,813,997 B2 | 10/2020 | Creighton |
| 11,000,589 B2 | 5/2021 | Creighton |
| 2001/0038683 A1 | 11/2001 | Ritter et al. |
| 2002/0019644 A1* | 2/2002 | Hastings ........ A61B 17/320758 606/41 |
| 2002/0072662 A1 | 6/2002 | Hall et al. |
| 2002/0100486 A1 | 8/2002 | Creighton et al. |
| 2002/0103426 A1 | 8/2002 | Segner et al. |
| 2002/0103430 A1 | 8/2002 | Hastings et al. |
| 2002/0115904 A1 | 8/2002 | Ren |
| 2003/0009094 A1 | 1/2003 | Segner et al. |
| 2003/0028071 A1 | 2/2003 | Handy et al. |
| 2003/0032995 A1 | 2/2003 | Handy et al. |
| 2003/0086867 A1 | 5/2003 | Lanza et al. |
| 2003/0105382 A1 | 6/2003 | Brown et al. |
| 2003/0181809 A1 | 9/2003 | Hall et al. |
| 2003/0220667 A1 | 11/2003 | Van Der Burg |
| 2004/0002654 A1 | 1/2004 | Davidson et al. |
| 2004/0006301 A1 | 1/2004 | Sell et al. |
| 2004/0006350 A1 | 1/2004 | Hogg et al. |
| 2004/0064153 A1 | 4/2004 | Creighton et al. |
| 2004/0077942 A1 | 4/2004 | Hall et al. |
| 2004/0096511 A1 | 5/2004 | Harburn et al. |
| 2004/0133118 A1 | 7/2004 | Llinas |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0186376 A1 | 9/2004 | Hogg et al. |
| 2004/0196127 A1 | 10/2004 | Perrin |
| 2004/0253183 A1 | 12/2004 | Uber, III et al. |
| 2004/0254419 A1 | 12/2004 | Wang et al. |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0025797 A1 | 2/2005 | Wang et al. |
| 2005/0033162 A1 | 2/2005 | Garibaldi et al. |
| 2005/0065435 A1 | 3/2005 | Rauch et al. |
| 2005/0079132 A1 | 4/2005 | Wang et al. |
| 2005/0090732 A1 | 4/2005 | Ivkov et al. |
| 2005/0113628 A1 | 5/2005 | Creighton et al. |
| 2005/0113812 A1 | 5/2005 | Viswanathan et al. |
| 2005/0119556 A1 | 6/2005 | Gillies et al. |
| 2005/0119687 A1 | 6/2005 | Dacey et al. |
| 2005/0182315 A1 | 8/2005 | Ritter et al. |
| 2005/0256398 A1 | 11/2005 | Hastings et al. |
| 2005/0271732 A1 | 12/2005 | Seeney et al. |
| 2005/0271745 A1 | 12/2005 | Gruettner et al. |
| 2005/0273130 A1 | 12/2005 | Sell |
| 2005/0281858 A1 | 12/2005 | Kloke et al. |
| 2006/0025675 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036163 A1 | 2/2006 | Viswanathan |
| 2006/0041181 A1 | 2/2006 | Viswanathan et al. |
| 2006/0094956 A1 | 5/2006 | Viswanathan |
| 2006/0142630 A1 | 6/2006 | Meretei |
| 2006/0142632 A1 | 6/2006 | Meretei |
| 2006/0142749 A1 | 6/2006 | Ivkov |
| 2006/0144407 A1 | 7/2006 | Aliberto et al. |
| 2006/0144408 A1 | 7/2006 | Ferry |
| 2006/0165805 A1 | 7/2006 | Steinhoff et al. |
| 2006/0228421 A1 | 10/2006 | Seeney et al. |
| 2006/0270948 A1 | 11/2006 | Viswanathan et al. |
| 2006/0276867 A1 | 12/2006 | Viswanathan |
| 2006/0278248 A1 | 12/2006 | Viswanathan |
| 2006/0281990 A1 | 12/2006 | Viswanathan et al. |
| 2007/0010702 A1 | 1/2007 | Wang et al. |
| 2007/0016010 A1 | 1/2007 | Creighton et al. |
| 2007/0016131 A1 | 1/2007 | Munger et al. |
| 2007/0021731 A1 | 1/2007 | Garibaldi et al. |
| 2007/0021744 A1 | 1/2007 | Creighton |
| 2007/0032746 A1 | 2/2007 | Sell |
| 2007/0038065 A1 | 2/2007 | Creighton et al. |
| 2007/0038074 A1 | 2/2007 | Ritter et al. |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0062546 A1 | 3/2007 | Viswanathan et al. |
| 2007/0135804 A1 | 6/2007 | Ritter et al. |
| 2007/0148634 A1 | 6/2007 | Bruchez et al. |
| 2007/0149946 A1 | 6/2007 | Viswanathan et al. |
| 2007/0167720 A1 | 7/2007 | Viswanathan et al. |
| 2007/0191671 A1 | 8/2007 | Kawano et al. |
| 2007/0197899 A1 | 8/2007 | Ritter et al. |
| 2007/0197906 A1 | 8/2007 | Ritter |
| 2007/0225589 A1 | 9/2007 | Viswanathan |
| 2007/0231393 A1 | 10/2007 | Ritter et al. |
| 2007/0250041 A1 | 10/2007 | Werp |
| 2007/0270686 A1 | 11/2007 | Ritter et al. |
| 2007/0287909 A1 | 12/2007 | Garibaldi et al. |
| 2008/0004595 A1 | 1/2008 | Viswanathan et al. |
| 2008/0006280 A1 | 1/2008 | Aliberto et al. |
| 2008/0015427 A1 | 1/2008 | Kastelein et al. |
| 2008/0016677 A1 | 1/2008 | Creighton |
| 2008/0039705 A1 | 2/2008 | Viswanathan |
| 2008/0039830 A1 | 2/2008 | Munger et al. |
| 2008/0045865 A1 | 2/2008 | Kislev |
| 2008/0047568 A1 | 2/2008 | Ritter et al. |
| 2008/0058608 A1 | 3/2008 | Garibaldi et al. |
| 2008/0058609 A1 | 3/2008 | Garibaldi et al. |
| 2008/0059598 A1 | 3/2008 | Garibaldi et al. |
| 2008/0064933 A1 | 3/2008 | Garibaldi et al. |
| 2008/0065061 A1 | 3/2008 | Viswanathan |
| 2008/0092993 A1 | 4/2008 | Creighton |
| 2008/0097200 A1 | 4/2008 | Blume et al. |
| 2008/0114335 A1 | 5/2008 | Flickinger et al. |
| 2008/0200913 A1 | 8/2008 | Viswanathan |
| 2008/0208912 A1 | 8/2008 | Garibaldi |
| 2008/0228065 A1 | 9/2008 | Viswanathan et al. |
| 2008/0228068 A1 | 9/2008 | Viswanathan et al. |
| 2008/0287909 A1 | 11/2008 | Viswanathan et al. |
| 2008/0294232 A1 | 11/2008 | Viswanathan |
| 2008/0312673 A1 | 12/2008 | Viswanathan et al. |
| 2009/0012821 A1 | 1/2009 | Besson et al. |
| 2009/0062646 A1 | 3/2009 | Creighton, IV et al. |
| 2009/0062828 A1 | 3/2009 | Marr |
| 2009/0082722 A1 | 3/2009 | Munger et al. |
| 2009/0105579 A1 | 4/2009 | Garibaldi |
| 2009/0131798 A1 | 5/2009 | Minar et al. |
| 2009/0131927 A1 | 5/2009 | Kastelein et al. |
| 2009/0138009 A1 | 5/2009 | Viswanathan et al. |
| 2009/0148387 A1 | 6/2009 | Bikram |
| 2009/0177032 A1 | 7/2009 | Garibaldi et al. |
| 2009/0285759 A1 | 11/2009 | Ishikawa et al. |
| 2009/0287036 A1 | 11/2009 | Shapiro et al. |
| 2009/0297441 A1 | 12/2009 | Canham et al. |
| 2009/0299127 A1 | 12/2009 | Rudolph et al. |
| 2009/0306643 A1 | 12/2009 | Pappone et al. |
| 2010/0003197 A1 | 1/2010 | Bikram |
| 2010/0055042 A1 | 3/2010 | Yathindranath et al. |
| 2010/0063385 A1 | 3/2010 | Garibaldi et al. |
| 2010/0069733 A1 | 3/2010 | Kastelein et al. |
| 2010/0097315 A1 | 4/2010 | Garibaldi et al. |
| 2010/0137706 A1 | 6/2010 | Viswanathan |
| 2010/0163061 A1 | 7/2010 | Creighton |
| 2010/0168553 A1 | 7/2010 | Martel |

(56) References Cited

U.S. PATENT DOCUMENTS

| | | |
|---|---|---|
| 2010/0204674 A1 | 8/2010 | Forbes et al. |
| 2010/0222669 A1 | 9/2010 | Flickinger et al. |
| 2010/0233147 A1 | 9/2010 | Schwartz et al. |
| 2010/0269838 A1 | 10/2010 | Flanagan et al. |
| 2010/0298845 A1 | 11/2010 | Kidd et al. |
| 2011/0021970 A1 | 1/2011 | Vo-Dinh et al. |
| 2011/0022029 A1 | 1/2011 | Viswanathan |
| 2011/0028989 A1 | 2/2011 | Ritter et al. |
| 2011/0046618 A1 | 2/2011 | Minar et al. |
| 2011/0071335 A1 | 3/2011 | Ueda et al. |
| 2011/0087237 A1 | 4/2011 | Viswanathan |
| 2011/0130718 A1 | 6/2011 | Kidd et al. |
| 2011/0152712 A1 | 6/2011 | Cao et al. |
| 2011/0215888 A1 | 9/2011 | Abbott et al. |
| 2011/0245581 A1 | 10/2011 | Schwartz et al. |
| 2012/0021010 A1 | 1/2012 | Deb et al. |
| 2012/0157824 A1 | 6/2012 | Bossmann et al. |
| 2012/0183475 A1 | 7/2012 | Michel et al. |
| 2012/0226093 A1 | 9/2012 | Creighton |
| 2012/0232329 A1 | 9/2012 | Creighton |
| 2012/0296149 A1 | 11/2012 | Creighton |
| 2012/0310034 A1 | 12/2012 | Creighton |
| 2013/0023714 A1 | 1/2013 | Johnston et al. |
| 2013/0296631 A1 | 11/2013 | Weinberg et al. |
| 2014/0135564 A1 | 5/2014 | Creighton |
| 2014/0163367 A1 | 6/2014 | Eskuri |
| 2014/0248632 A1 | 9/2014 | Kopelman et al. |
| 2015/0099919 A1 | 4/2015 | Creighton |
| 2015/0230810 A1 | 8/2015 | Creighton et al. |
| 2015/0231282 A1 | 8/2015 | Pozzo et al. |
| 2015/0366574 A1 | 12/2015 | Kovarik et al. |
| 2015/0374395 A1 | 12/2015 | Creighton |
| 2017/0095675 A1 | 4/2017 | Creighton |
| 2017/0128571 A1 | 4/2017 | Creighton |
| 2017/0165020 A1 | 6/2017 | Martel |
| 2018/0221041 A1 | 8/2018 | Creighton et al. |
| 2019/0069922 A1* | 3/2019 | McCarthy ...... A61B 17/320758 |
| 2019/0336231 A1 | 11/2019 | Kidd et al. |
| 2020/0085730 A1 | 3/2020 | Khizroev et al. |
| 2020/0330727 A1 | 10/2020 | Creighton |
| 2020/0330730 A1 | 10/2020 | Creighton |
| 2020/0360711 A1 | 11/2020 | Kidd et al. |
| 2021/0093339 A1 | 4/2021 | Creighton |

FOREIGN PATENT DOCUMENTS

| | | |
|---|---|---|
| EP | 1001811 B1 | 9/2002 |
| JP | H07(1995)-500278 A | 1/1995 |
| JP | H07-213622 A | 8/1995 |
| JP | 2011-501751 A | 1/2011 |
| WO | WO 89/10788 | 11/1989 |
| WO | WO 2003/022360 | 3/2003 |
| WO | WO 2004/083902 A2 | 9/2004 |
| WO | WO 2005/011810 | 2/2005 |
| WO | WO 2005/072169 | 8/2005 |
| WO | WO 2006/035550 | 4/2006 |
| WO | WO 2007/125699 | 11/2007 |
| WO | WO 2008/95450 A | 8/2008 |
| WO | WO 2010/092495 | 8/2010 |
| WO | WO 2011/047313 | 4/2011 |
| WO | WO 2011/050085 | 4/2011 |
| WO | WO 2011/053984 | 5/2011 |
| WO | WO 2012/009675 | 1/2012 |
| WO | WO 2012/018290 | 2/2012 |
| WO | WO 2013/185032 | 12/2013 |
| WO | WO 2016/069982 | 5/2016 |

OTHER PUBLICATIONS

Chen, Haitao, et al., "Capture of Magnetic Carriers Within Large Arteries Using External Magnetic Fields," Journal of Drug Targeting, May 2008, 16:4,262-268.

Grady, M.S. et al., "Nonlinear Magnetic Stereotaxis: Three-Dimensional, In Vivo Remote Magnetic Manipulation of A Small Object In Canine Brain," Medical Physics, vol. 17, No. 3, May/Jun. 1990, pp. 405-415.

Gupta, Ajay K. et al., "Synthesis And Surface Engineering of Iron Oxide Nanoparticles for Biomedical Applications," Biomaterials, vol. 26, Issue 18, Jun. 2005, pp. 3995-4021.

Leadley, Robert J. Jr., et al., "Contribution of In Vivo Models of Thrombosis to the Discovery and Development of Novel Antithrombotic Agents," Journal of Pharmacological and Toxicological Methods, Mar.-Apr. 2000, pp. 101-116, vol. 43, Issue 2.

Peasley, K.W., "Destruction of Human Immunodeficiency-Infected Cells by Ferrofluid Particles Manipulated by an External Magnetic Field: Mechanical Disruption and Selective Introduction of Cytotoxic or Antiretroviral Substances into Target Cells," Medical Hypothesis, Jan. 1996, pp. 5-12, vol. 46, Issue 1.

Pouliquen, D. et. al., "Iron Oxide Nanoparticles for Use as an MRI Contrast Agent: Pharmacokinetics and Metabolism," Magnetic Resonance Imaging, 1991, pp. 275-283, vol. 9, Issue 3.

Sugimoto, Tadao, Egoa Matijevic, "Formation of Uniform Spherical Magnetite Particles by Crystallization from Ferrous Hydroxide Gels," Journal of Colloid and Interface Science, Mar. 1980, pp. 227-243, vol. 74, Issue 1.

Wu, Sau-Ching, et al., "Functional Production and Characterization of a Fibrin-Specific Single-Chain Antibody Fragment from Bacillus Subtilis: Effects of Molecular Chaperones and a Wall-Bound Protease on Antibody Fragment Production," Applied and Environmental Microbiology, Jul. 2002, p. 3261-3269, American Society for Microbiology, 2002.

Yodh, Shyam B. et al., "A New Magnet System for Intravascular Navigation", Med. & Biol. Engng., vol. 6, pp. 143-147 (1968).

Cheng, Rui et al., "Acceleration of Tissue Plasminogen Activator Mediated Thrombolysis by Magnetically Powered Nanomotors," ACS Nano, Jul. 9, 2014, downloaded from https://pubs.acs.org on Jul. 13, 2014.

Houston Methodist. "Magnetic nanoparticles could stop blood clot-caused strokes." Newswise, Inc. Feb. 23, 2015. < http://www.newswise.com/articles/magnetic-nanoparticles-could-stop-blood-clot-caused-strokes>.

Chen, Jyh-Ping et al., Targeted delivery of tissue plasminogen activator by binding to silica-coated magnetic nanoparticle, International Journal of Nanomedicine, Sep. 26, 2012, pp. 5137-5149.

Yang et al., Bioconjugation of recombinant tissue plasminogen activator to magnetic nanocarriers for targeted thrombolysis, International Journal of Nanomedicine, Sep. 28, 2012, pp. 5159-5173.

Sun et al., Magnetic nanoparticle in MR Imagining and drug delivery; Advanced Drug Delivery Reviews, 60(11): p. 1252-1265, Aug. 2008.

Yathindranath, V., et al. Simultaneous magnetically directed drug convection and MR imaging, Nanotechnology 20(40): paper #405101, 12 pgs. Sep. 2009.

Rosengart, A.J., et al., Magnetically Guided Plasminogen Activator-Loaded Designer Spheres for Acute Stroke Lysis, Medical Hypotheses and Research, 2(3): p. 413-424, Jul. 2005.

Ci Acar HY, et al., Superparamagnetic nanoparticles stabilized by polymerized PEGylated coatings, Journal of magnetism and magnetic materials, 293(1):p. 107, May 2005.

Torno, MD, et al., Improvement of in vitro thrombolysis employing magnetically-guided microspheres, Thrombosis Research, 121(6): p. 799-811, Jan. 2008.

Drozdov, Andrey et al., Leach-proof magnetic thrombolytic nanoparticles and coatings of enhanced activity, published Jun. 20, 2016; Scientific Reports; pp. 1-8.

El-Sherbiny, Ibrahim et al., Tissue plasminogen activator-based clot busting: Controlled delivery approaches, Global Cardiology Science & Practice, Sep. 2014; pp. 337-349.

Friedrich, Ralf et al., Tissue Plasminogen Activator Binding to Superparamagnetic Iron Oxide Nanoparticle, Nanoscale Research Letters; 2016, pp. 1-11.

Hsu, Hao-Lung et al., Preparation of thermosensitive magnetic liposome encapsulated recombinant tissue plasminogen activator for targeted thrombolysis, Journal of Magnetism and Magnetic Materials, Oct. 2017, pp. 188-194.

(56) References Cited

OTHER PUBLICATIONS

Hu, Jiangnan et al., Magnetically active Fe3O4 nanorods loaded with tissue plasminogen activator for enhanced thrombolysis, Nano Research, 2016, pp. 2562-2661.

Voros Eszter et al., TPA Immobilization on Iron Oxide Nanocubes and Localized Magnetic Hyperthermia Accelerate Blood Clot Lysis, Advanced Functional Materials Journal, 2015, pp. 1709-1718.

\* cited by examiner

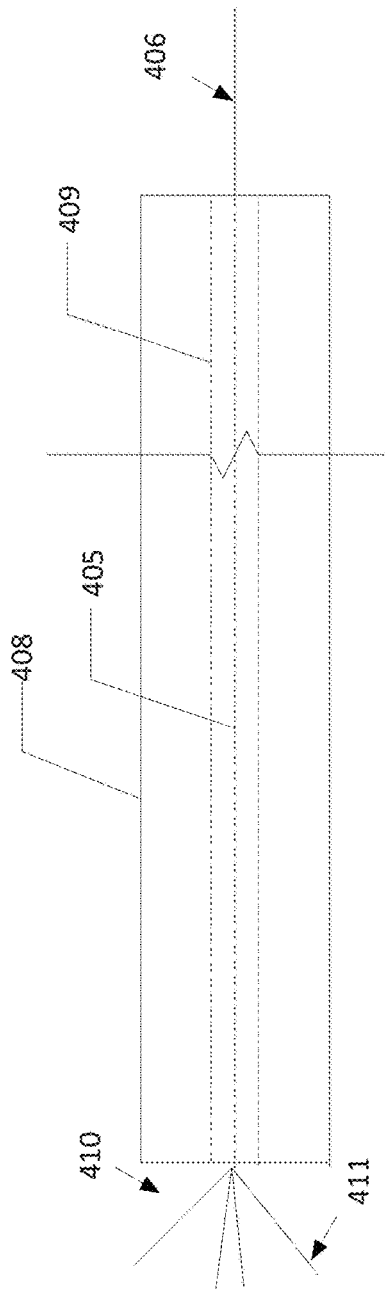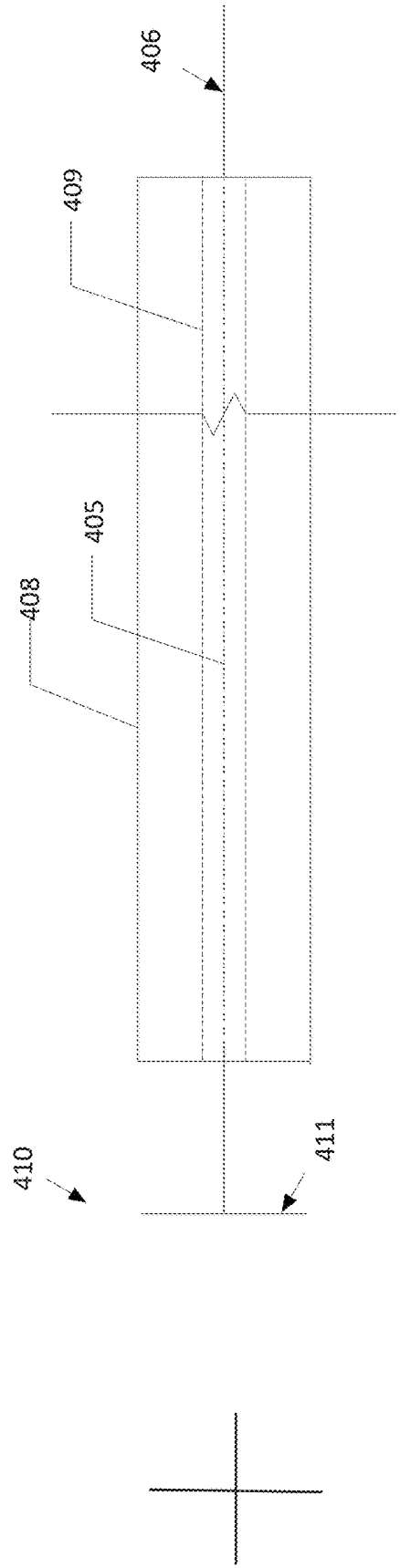
FIGURE 4C
FIGURE 4D
FRONT VIEW

MAGNETICALLY CONTROLLED FLOW GENERATION

RELATED APPLICATIONS

This application claims priority to U.S. Provisional Application No. 63/200,476 filed Mar. 9, 2021, the entire content of which is hereby incorporated herein by reference. This application is related to WIPO Publ. No. WO 2019/108536 published Jun. 6, 2019 and US Publ. No. 2019/0336231 published on Nov. 7, 2019, the entire content of each of which is hereby incorporated herein by reference.

FIELD

This disclosure generally relates to systems and methods for facilitating flow within vasculature or other body lumens, channels or passages involving a magnetic field generated by an external magnetic control system and/or facilitating clearance of obstructions (e.g., clots, fluid obstructions) within in-dwelling devices (e.g., shunts, drains, conduits, ports, catheters) involving magnetic particles (e.g., nanoparticles, microparticles) controlled by an external magnetic control system (e.g., one or more rotating permanent magnets or an electromagnetic control system).

SUMMARY

In accordance with several embodiments, a method of facilitating treatment of a therapeutic target within a body of a subject includes delivering a magnetically-responsive flow generator to a location adjacent the therapeutic target. The magnetically-responsive flow generator includes an elongate wire or shaft having a proximal end and a distal end. The elongate wire does not comprise magnetically-responsive material. For example, the elongate wire may be formed of a non-magnetic material (e.g., non-ferrous metal or a biocompatible polymer). The magnetically-responsive flow generator also includes a rotor rotatably coupled to the proximal end of the elongate wire. The rotor comprises magnetically-responsive material. For example, the rotor may comprise magnetic material such as iron oxide or other ferrous metal substance. The rotor is configured to rotate about a central longitudinal axis of the elongate wire upon application of a rotating magnetic field (e.g., generated by a magnetic controller external to the body of the subject) while the elongate wire remains stationary. The method also includes applying a rotating magnetic field from outside the body of the subject so as to cause the rotor to rotate. Rotation of the rotor generates fluid flow toward the therapeutic target.

Delivering the magnetically-responsive flow generator to the location adjacent the therapeutic target may include inserting the magnetically-responsive flow generator into a lumen of a catheter and advancing the magnetically-responsive flow generator along the lumen of the catheter until the rotor of the magnetically-responsive flow generator exits the lumen of the catheter. In other implementations, the rotor remains in the lumen of the catheter.

Applying the rotating magnetic field may include causing rotation of at least one permanent magnet (e.g., one permanent magnet, two or more permanent magnets) of an external magnetic control system. Alternatively, applying the rotating magnetic field may include generating a rotating magnetic field with an electromagnet of an external magnetic control system.

The rotor may include a propeller having a rotating hub with a plurality of blades or other outwardly-extending members. The plurality of blades or other outwardly-extending members may not comprise any sharpened surfaces. However, in some embodiments, the plurality of blades or other outwardly-extending members may comprise abrasive material or a sharpened surface. The rotor may be formed of shape memory material that is adapted to transition to a default, expanded (e.g., self-expanded) configuration when unconstrained. The rotor may be adapted to rotate in a first rotational direction to generate flow (e.g., "pushing" flow) in a first direction and to rotate in a second rotational direction to generate flow in an opposite second direction (e.g., "pulling" or "siphoning" flow).

The therapeutic target may be, for example, a clot within a blood vessel, an obstruction within an in-dwelling device, an obstruction within a body lumen, a chronic total occlusion within a blood vessel, a stenotic lesion within a blood vessel, cancerous tissue, or a region of low fluid flow.

In accordance with several embodiments, a magnetically-responsive flow generator configured to generate flow at a location adjacent a therapeutic target within a subject includes an elongate wire or shaft having a proximal end and a distal end. The magnetically-responsive flow generator includes a rotor rotatably coupled to the proximal end of the elongate wire. The rotor comprises magnetically-responsive material. The rotor is configured to rotate about a central longitudinal axis of the elongate wire in response to application of a rotating magnetic field while the elongate wire remains stationary. The rotating magnetic field is generated by a magnetic control system positioned external to the subject. The elongate wire does not comprise magnetically-responsive material.

The rotor may comprise shape memory material (e.g., nickel-titanium alloy). The rotor may be configured to self-expand into a default, expanded configuration when unconstrained (e.g., by a catheter or sheath). The rotor may include multiple outwardly-extending members sized and shaped to generate flow upon rotation of the rotor in response to application of the magnetic field.

In accordance with several embodiments, a method of facilitating clearance of an obstruction within a brain shunt includes introducing a plurality of magnetic particles within a lumen of the brain shunt, and applying a rotating magnetic field using a permanent magnet positioned external to the subject so as to cause the magnetic particles to agglomerate into stir bars and to travel in a rotating end-over-end motion toward the obstruction. The rotating end-over-end motion of the stir bars causes circulating fluid motion to facilitate clearance of the obstruction.

The brain shunt may be any other in-dwelling catheter, tube, shunt, implant, or device (temporary or permanent). The method may also include delivering one or more therapeutic agents adapted to clear the obstruction into the lumen of the brain shunt, wherein the rotating end-over-end motion of the stir bars causes the one or more therapeutic agents to travel toward the obstruction.

The magnetic particles may comprise a therapeutic agent configured to cause breakdown or lysis of the obstruction. The method may also include imaging the stir bars or the motion of the stir bars so as to identify a location of the obstruction.

The methods summarized above and set forth in further detail below may describe certain actions taken by a practitioner; however, it should be understood that they can also include the instruction of those actions by another party. For example, actions such as "advancing a device" include "instructing the advancement of a device." Further aspects of embodiments of the inventions will be discussed in the following portions of the specification. With respect to the drawings, elements from one figure may be combined with elements from the other figures.

BRIEF DESCRIPTION OF THE DRAWINGS

The drawings, which are briefly described below, are for illustrative purposes only. The drawings are not intended to limit the scope of the disclosure in any way and may not be to scale.

FIGS. 4A-4E schematically illustrate an embodiment, and operation, of a magnetically responsive flow generator configured to respond to a magnetic control system positioned external to a body of a subject.

DETAILED DESCRIPTION

Abbreviations and Definitions

Figure 1:
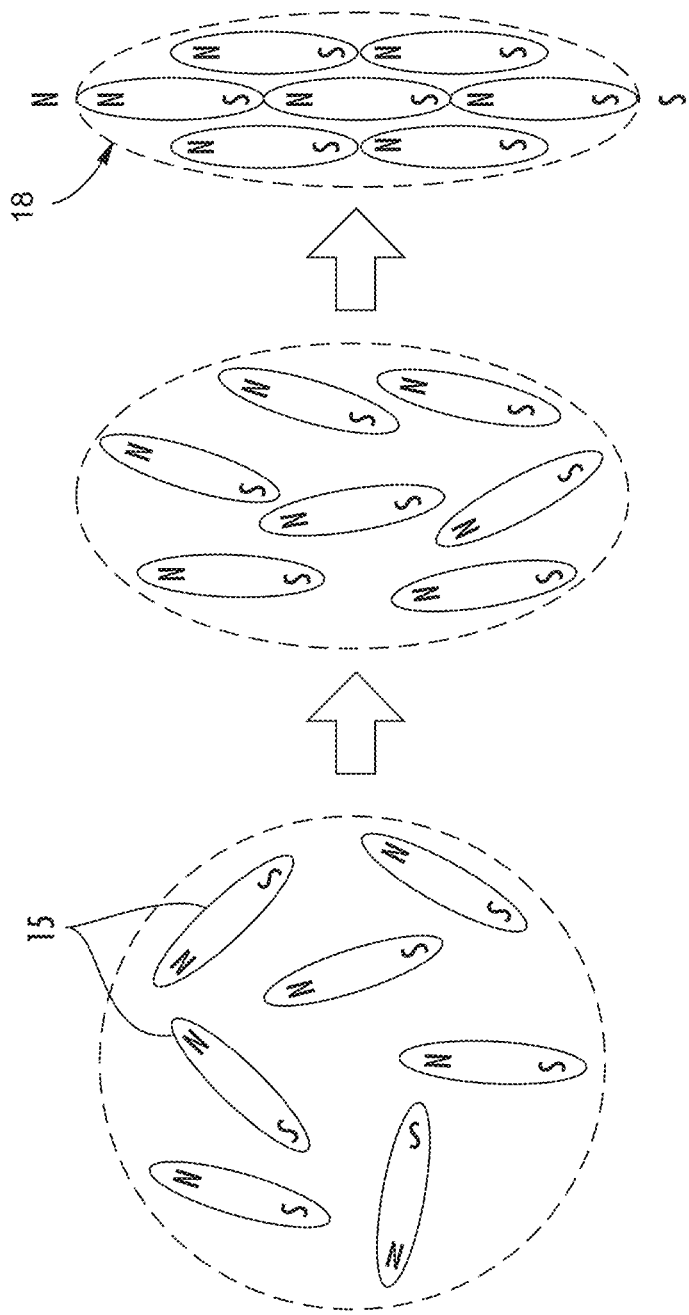
FIG. 1 schematically illustrates a sequence showing agglomeration of magnetic particles into an agglomerated structure under the influence of an applied magnetic field.

The scientific and technical terms used in connection with the disclosure shall have their ordinary meanings (e.g., as commonly understood by those of ordinary skill in the art) in addition to any definitions included herein. Further, unless otherwise required by context, singular terms shall include pluralities and plural terms shall include the singular.

"Patient" or "subject" shall be given its ordinary meaning and shall include, without limitation, human and veterinary subjects.

"Therapeutic agents" shall be given its ordinary meaning and shall include, without limitation, drugs or compositions capable of degrading a blood clot or atherosclerotic plaque (e.g., chronic total occlusion). For example, a thrombolytic drug can include tissue plasminogen activator (tPA), plasminogen, streptokinase, urokinase, recombinant tissue plasminogen activators (rtPA), alteplase, reteplase, tenecteplase, collagenase, and other drugs, and can include these drugs administered alone or co-administered with warfarin and/or heparin. Different thrombolytic drugs can be used in the thrombolytic process for different types of occlusions. Therapeutic agents may comprise a structure (e.g., composition) configured to deliver a payload to a therapeutic or diagnostic target (e.g., cancerous tissue, a site of infection, a diagnostic imaging target). The payload could include an anti-inflammatory agent.

"Magnetic particle" shall be given its ordinary meaning and shall include, without limitation, magnetic nanoparticles having a diameter greater than or equal to about 1 nm and/or less than or equal to about 1000 nm, greater than or equal to about 10 nm and/or less than or equal to about 200 nm, greater than or equal to about 15 nm and/or less than or equal to about 150 nm, greater than or equal to about 20 nm and/or less than or equal to about 60 nm, 80 nm, 100 nm, and all integer values between 1 nm and 1000 nm, e.g., 1, 2, 3, 4, 5 . . . . 997, 998, 999, and 1000. Magnetic particles may also include microparticles having a diameter greater than 1000 nm. The appropriate sizes of magnetic particles can depend on the therapeutic target of the system (e.g., very small vessels can accept smaller nanoparticles and larger parts of a circulatory system can accept larger nanoparticles). Examples of such magnetic nanoparticles include ferrimagnetic iron oxide nanoparticles. The particles may be made of magnetite or iron oxide and, in some embodiments, can be co-administered, coated or conjugated with one or more of the following: (1) diagnostic agents which allow visualization with an imaging modality (e.g., magnetic resonance imaging, X-ray, Positron Emission Tomography (PET), ultrasound, fluoroscopy, magnetic localization, computed tomography imaging (CT) or other imaging technologies; (2) therapeutic agents adapted to treat a therapeutic target (e.g., a circulatory system blockage, occlusion, obstruction, clot); and (3) theranostic agents adapted to provide both therapeutic and diagnostic capabilities.

"Fluid obstruction" shall be given its ordinary meaning and shall include, without limitation, a blockage, either partial or complete, that impedes the normal flow of fluid through the circulatory system (including the venous system and arterial system), the central nervous system, and the lymphatic system. "Vascular occlusions" are fluid obstructions that include, but are not limited to, atherosclerotic plaques, fatty buildup, fibrous caps, arterial stenosis, chronic total occlusion areas, restenosis, vein thrombi, cerebral thrombi, embolisms, hemorrhages, other blood clots, and very small vessels. Sometimes, fluid obstructions are generally referred to herein as "clots." The occlusions may completely or partially block flow through a vessel. Therapeutic targets, obstructions, and occlusions are considered to be used interchangeably in several embodiments described herein.

"Contrast Agent" and "Contrast Media" shall be given their ordinary meaning and shall include, without limitation, any material (solid or liquid) that facilitates visualization or imaging utilizing any imaging modality. Contrast media can be any substance used to enhance the contrast of structures or fluids within the body in medical imaging. The contrast media can include, for example, contrast agents, iodinated contrast media, ionic iodinated contrast media, lymphatic staining agents, magnetic resonance imaging contrast media, miscellaneous diagnostic dyes, non-iodinated contrast media, non-ionic iodinated contrast media, ultrasound contrast media, iodine, barium, gadolinium, ethiodoized oil, gadoterate meglumine, iodixanol, iohexol, microbubble contrast agents, radiopharmaceuticals, and/or any other contrast media. The contrast media may be delivered directly or locally to a target location through a catheter such as described herein, through systemic intravenous introduction, nasally, rectally, vaginally, orally, through inhalation to the lung, and by injection into muscle or skin or underneath the skin.

"Theranostic Agent" shall be given its ordinary meaning and shall include, without limitation, any material (solid or liquid) that provides combined therapeutic and diagnostic capabilities or effects. Theranostic agents may include any agents configured to simultaneously facilitate both therapy and diagnosis (e.g., radioiodine, biologics, iron oxide nanoparticles, quantum dots, carbon nanotubes, gold nanoparticles, and silica nanoparticles).

"Agglomerate" shall be given its ordinary meaning and shall include, without limitation, rotational clustering and chaining of a group of individual magnetic particles (e.g., nanoparticles, microparticles) in a manner to form "stir bars"

or "stir rods" from the magnetic particles, as well as the combined structures themselves when used as a noun.

"Treatment" shall be given its ordinary meaning and shall include, without limitation, an approach for obtaining beneficial or desired clinical results. For purposes of this disclosure, beneficial or desired clinical results include, but are not limited to, one or more of the following: improvement or alleviation of any aspect of fluid obstruction within a body of a subject or within a device including, but not limited to, conditions caused by fluid obstructions (e.g., stroke, deep vein thrombosis, chronic total occlusion, myocardial infarction, pulmonary embolisms), coronary artery disease (e.g., chronic total occlusion), peripheral vascular disease (e.g., peripheral artery disease, venous thromboembolism, deep venous thrombosis, superficial venous disease), ischemic heart disease, atherosclerosis, and high blood pressure; cancer treatment, diseases of the cerebro-spinal fluid, lymphatic disease, micro-circulatory disease; or movement along any body lumen, space, or cavity to access a desired treatment, or therapeutic, or diagnostic imaging target.

Several embodiments of the inventions are particularly advantageous because they include one, several or all of the following benefits: (i) clearing of obstructions or blockages from in-dwelling devices (e.g., catheters, tubes or shunts) without requiring removal or replacement of the devices; (ii) do not require an active control mechanism mechanically coupled to a rotor to rotate within a blood vessel or bodily lumen to generate fluid flow; (iii) require less real estate (e.g., cross-sectional area or volume) of a catheter (e.g., microcatheter or guide catheter) while still facilitating generation of fluid flow distal to the catheter; and/or (iv) the ability of contrast agent/media or guidewires or other instruments to traverse through occlusions (e.g., chronic total occlusions) that could not be traversed otherwise.

Magnetic Particles and Magnetic Control Systems

Systems and methods for the physical manipulation of magnetic particles (e.g., nanoparticles) within body lumens (e.g., vasculature) of a subject to facilitate treatment of therapeutic targets (e.g., clearance of fluid obstructions) are described and illustrated in WIPO Publication No. WO 2011/053984, WIPO Publ. No. WO 2013/173235, WIPO Publ. No. WO 2019/108536, and US Publ. No. 2019/0336231, the entire contents of each of which are hereby incorporated by reference herein. The embodiments disclosed herein may be combined with and incorporated in conjunction with any of the embodiments or features of the magnetic control systems, therapeutic targets, or imaging or diagnostic methods disclosed in WIPO Publication No. WO 2013/173235, the entire contents of each of which are hereby incorporated by reference herein. For example, FIGS. 1, 2A-2C and 3 included herein are from WIPO Publ. No. WO 2013/173235 to illustrate such example systems and methods.

When a magnetic field is imposed on, or applied to, a collection of magnetic particles (e.g., nanoparticles), they can combine, or assemble, to form larger structures (e.g., agglomerates or agglomerated structures or ensembles or stir bars or stir rods). The size of these assembled structures can be related to an applied magnetic field strength, a size of the magnetic particles (e.g., nanoparticles), and/or a thickness of an optional coating on the magnetic particles (e.g., nanoparticles). FIG. 1 illustrates agglomeration of magnetic particles 15 into an assembled structure (e.g., a stir rod or stir bar or spheroid) 18 as a result of the applied magnetic field by the magnetic control system 10. The magnetic particles 15 can become magnetized and align due in part to the applied magnetic field. As the applied magnetic field increases in strength, the magnetic particles 15 can continue to become magnetized and align, assembling into a larger structure, such as the rod 18 depicted in FIG. 1. At a certain rotating magnetic field strength and field rotation frequency, depending on particle size and optional coating, the stir bars 18 will reach a saturation field and achieve a maximum length and/or width. In one embodiment, for uncoated magnetite particles, the particles are close to a saturation point when the applied magnetic field is approximately 0.2 T. In some embodiments, particle size can affect the strength and/or rigidity of the assembled structure. For example, when an assembled structure has an angular momentum, a likelihood that the assembled structure (e.g., stir bar) 18 will break apart is inversely related to the size of the magnetic particles 15 (e.g., nanoparticles) making up the assembled structure 18. Fully developed agglomerates 18 may contain a number of particles (e.g., nanoparticles), such as as many as ten or many more, depending on their size, and the magnitude of the rotating magnetic field. The agglomerates 18 are not stiff, depending on the magnetic field and gradient, and on the amount of magnetite or other ferrous core in each particle 15 as well as the particle size.

In one example, a field of about 0.02 Tesla at the target site, in combination with a gradient of about 0.4 Tesla/meter, can create an agglomeration of magnetic particles (e.g., separated nanoparticle "stir rods" or "stir bars"). In general, the agglomerated structures (e.g., stir rods or stir bars) 18 can have a length that is greater than or equal to about 0.05 mm and/or less than or equal to about 3 mm in length, including but not limited to from about 0.05 mm to about 2 mm, from about 0.1 mm to about 2 mm, from about 0.2 mm to about 1.5 mm, from about 0.2 mm to about 1 mm, from about 0.3 mm to about 0.9 mm, from about 0.4 mm to about 0.8 mm, overlapping ranges thereof, less than 3 mm, less than 2 mm, less than 1.5 mm, less than 1 mm.

Figure 2A:
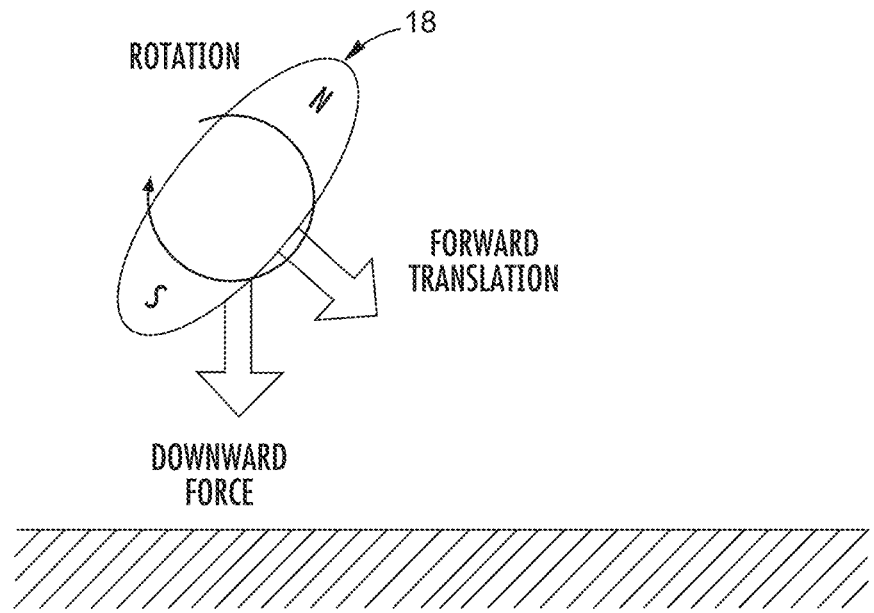
FIGS. 2A and 2B schematically illustrate an agglomerated structure rotating and translating as a result of a time-varying magnetic field and a gradient.

FIG. 2A illustrates an assembled structure 18, such as a stir rod or stir bar, rotating and translating as a result of a time-varying magnetic field applied by the magnetic control system 10. In some embodiments, the time-varying magnetic field 10 can rotate and can have a magnetic field gradient. This combination can result in a torque and a net force on the agglomerated structure. Due in part to the torque, the stir rod or stir bar 18 can rotate. The rotation and the net force can result in a forward translation of the agglomerated structure 18 as illustrated.

Figure 2B:
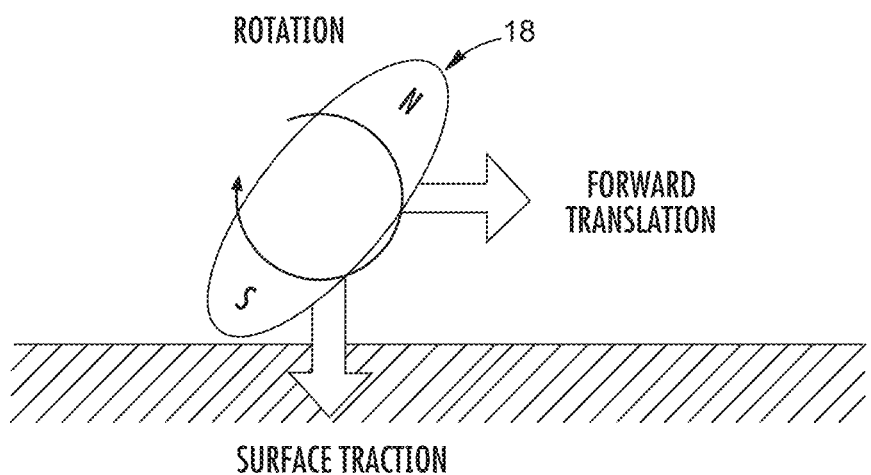

FIG. 2B illustrates an agglomerated structure 18 rotating and translating across a surface as a result of a time-varying magnetic field. If the agglomerated structure 18 comes into contact with a surface, a combination of the torque, force from the magnetic gradient, and friction between the agglomerated structure 18 and the surface can result in a forward translation. The motion of the agglomerated structure 18 can be end-over-end, similar to an ellipse or spheroid rolling along a surface.

As described with respect to FIGS. 2A and 2B, the agglomerated structure 18 can rotate and translate as a result of a time-varying magnetic field having a gradient. The stir rod or stir bar 18 can rotate and translate in a forward direction when in contact with a surface, to the right in FIG. 2B. Due in part to the rotation and translation of the agglomerated structures 18, a flow can be generated in a surrounding fluid, thereby generating micro-currents. As the agglomerated structure 18 moves (e.g., translates) forward it can experience a change in magnetic field. In some embodiments, the magnetic field can diminish with translation distance. As the gradient diminishes, the downward force on the agglomerated structure 18 can diminish. If the force diminishes past a threshold value, the agglomerated structure 18 can cease to be in contact with the surface, resulting in no friction force between the surface and the structure 18. The structure 18 can then experience a pressure arising from a flow of the fluid medium which surrounds the structure 18. This flow can result in a translation that is roughly backward, or left in FIG. 2B. As the structure 18 moves backward, the magnetic field gradient which the structure 18 experiences can increase and the structure 18 can be pulled back to the surface. Once back to the surface, the structure 18 can move forward in an end-over-end manner as explained above. The overall motion of the structure 18 can be generally circular or elliptical in nature. The end-over-end motion can facilitate travel of the structures 18 over complex terrains or surfaces within a patient's body.

Figure 2C:
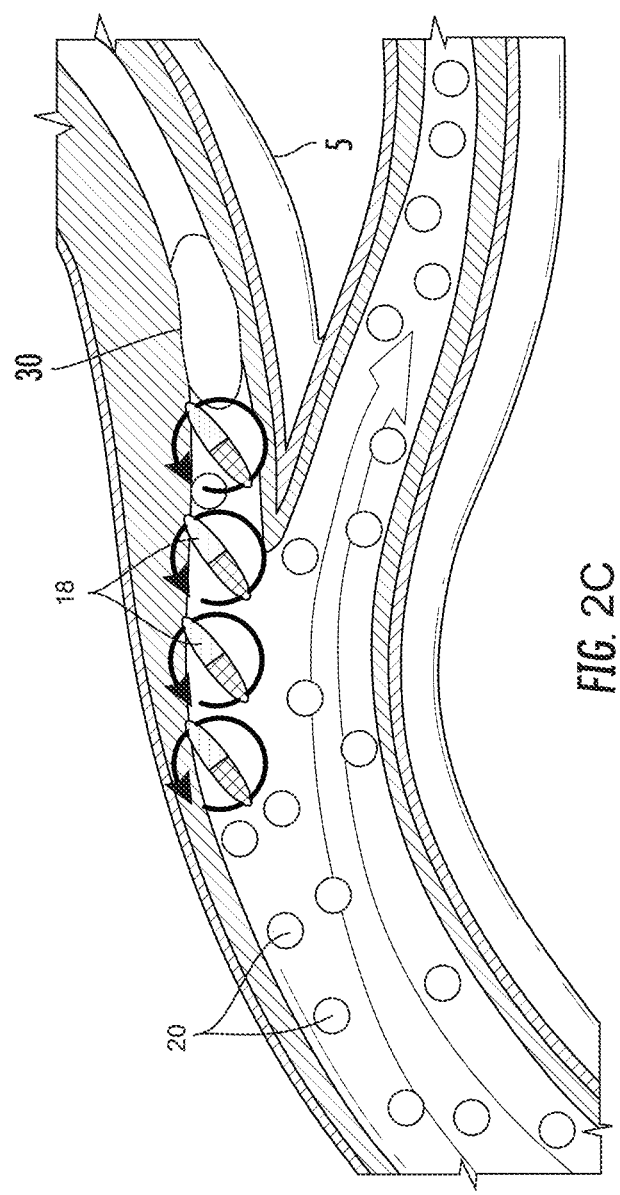
FIG. 2C schematically illustrates movement of multiple agglomerated structures toward a clot within a blood vessel.

With reference to FIG. 2C, in some embodiments, this flow pattern can increase mixing of a therapeutic and/or diagnostic agent (e.g., a thrombolytic, plasminogen, contrast agent, and/or theranostic agent or compound) or increase exposure of a therapeutic target 30 (e.g., a clot, a tumor) to a therapeutic agent. The micro-currents may also facilitate removal of debris from within one or more channels 40 of an obstruction 30. In some aspects, the fluid can be a mixture of blood and a therapeutic agent (e.g., a thrombolytic drug), the blood and therapeutic agent being mixed by the generally circular motion of the agglomerated structures 20 to erode (e.g., lyse) and clear the therapeutic target 30. FIG. 2C illustrates how the movement of the agglomerated structures 18 can cause thrombolytic particles 20 to be "carried" or transported toward a fluid obstruction (e.g., clot) 30 even when there is little or no flow in a portion of a branch vessel 35 adjacent to the fluid obstruction 30.

By alternating a rotational direction of the magnetic stator system and/or by changing a polarity of the one or more magnets or electromagnets creating the magnetic field, the operator can direct the agglomerated structures (e.g., magnetic rotors) 18 within a vessel 35. For example, within a vessel, a velocity of blood increases with distance from the vessel wall, where the velocity is approximately zero. A clotted vessel branch will obstruct fluid flow resulting in the velocity dropping to zero at the opening of the branch. Within such low or no-flow velocity regions, magnetic particles 15 generally assemble to be controlled by the magnetic stator system 10. When assembled, the magnetic stator system 10 can agglomerate the magnetic nanoparticles into larger structures 18 (e.g., magnetic rotors having an oblong shape). With a varying magnetic field, the magnetic rotors 18 can rotate, resulting in an end-over-end motion that results in the magnetic rotors traveling into or next to the blocked branches. The resulting rotational motion of the magnetic rotors can create new currents or increase low-velocity currents. The resulting circulating fluid currents can concentrate a therapeutic agent in an otherwise inaccessible or difficult to access region. By changing the rotation of the magnetic stator system 10, additional branches can be infused. For example, different rotational directions can result in the magnetic rotors 18 traveling to different branches. Rotational directions and/or magnetic polarities can be alternated to direct, or steer, magnetic rotors 18 to multiple branches. In accordance with several embodiments, the magnetic rotors need not contact the therapeutic target 30 to treat (e.g., reduce, erode, clear, or otherwise address) the target. For example, the magnetic rotors 18 can facilitate treatment (e.g., removal or erosion) of a thrombus or clot without scraping or contacting the clot or occlusion. In some embodiments, the magnetic rotors 18 infiltrate the target 30 (e.g., tumor) and deliver attached payload to the target 30.

Figure 3:
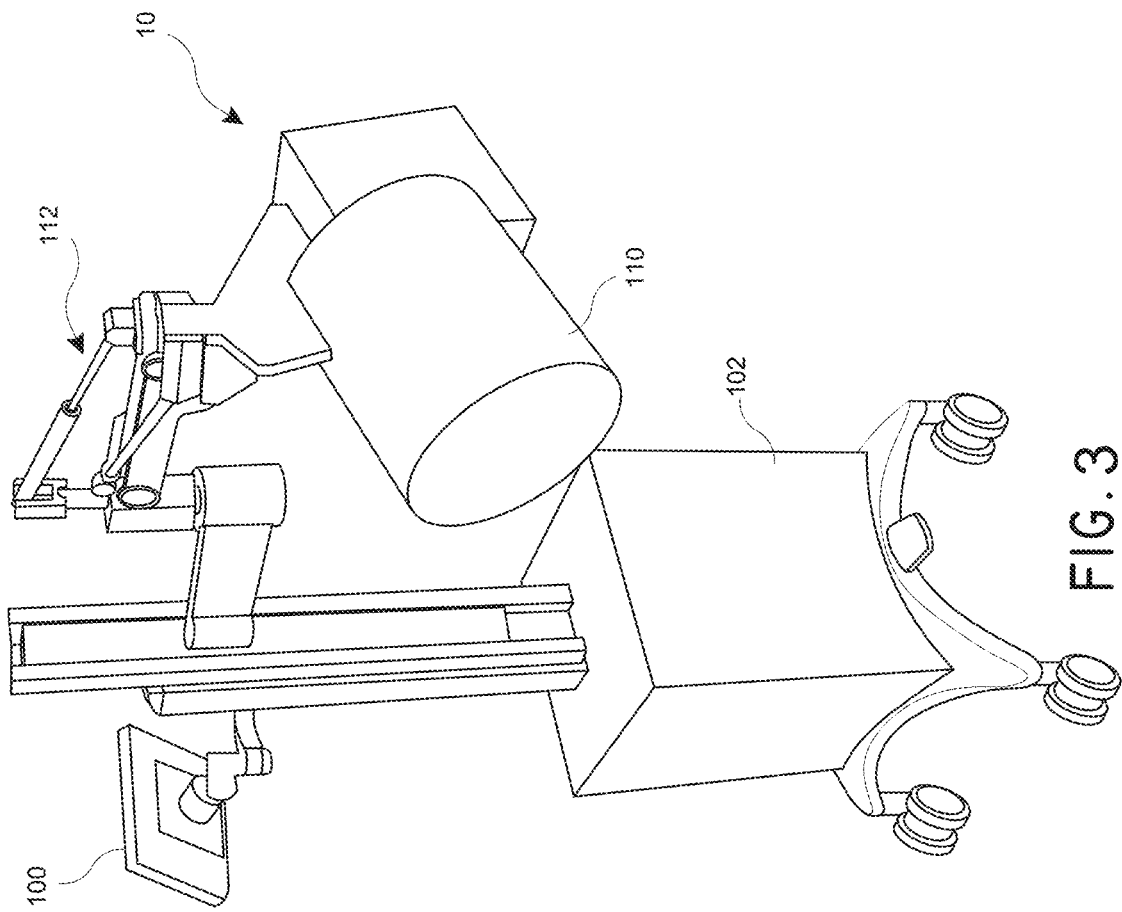
FIG. 3 illustrates an example of a magnetic control system in accordance with various implementations.

FIG. 3 illustrates an example of a magnetic control system 10 in accordance with various implementations. The magnetic control system 10 can include a portable support base 102 and an arm positioner 112, as illustrated in FIG. 3. The system 10 can include a magnetic stator system configured to produce a desired magnetic field. For example, a magnetic stator system can include a neodymium-iron-boron permanent magnet block connected to a shaft and yoke assembly. In some embodiments, the yoke assembly is machined using carbon fiber plates to decrease weight and improve performance.

The permanent magnet block can be a single permanent magnet or multiple magnets. For example, the permanent magnet block can comprise two, three, four, six, eight, or some other number of NdBFe50 medium-temperature 2 inch cubes. A mechanical drive train can connect these assemblies to a pair of electric motors configured to vary in angulation and time to vary the magnetic field produced by the magnetic block. In some embodiments, the magnetic block can have a rotational frequency of at least about 1, 2 or 3 Hz and/or less than or equal to about 10 Hz (e.g., 2-4 Hz, 1-5 Hz, etc.) to produce a desired varying magnetic field. In some embodiments, the magnetic block is configured to produce a desired magnetic field at least about 6 inches from the surface of the magnetic block. In some embodiments, the magnetic block is configured to produce a magnetic field that is less than or equal to about 5 Gauss at about 54.6 cm inches from the magnetic block, and/or less than or equal to about 1 Gauss at about 94 cm from the block. In several embodiments, these mechanisms are housed in a protective cover that protects the operator and patient from mechanical hazards, as well as protects the elements and assemblies contained within the housing from hazards outside the housing.

The arm positioner 112 can be configured to position and/or orient the magnetic control system 10 in a desired location, such as adjacent to a patient's head, during treatment, or into a stowed position when not in use. The system 10 can include mechanisms to substantially secure the magnetic stator system in a desired location, such as locking or friction mechanisms. The system 10 can advantageously include a touchscreen interface module 100 configured to display information to the operator and receive input from the operator for use in controlling the system.

Positioning the magnet pod or block 110 of the magnetic control or stator system 10 can include using one or more mechanical features, e.g., the positioning assembly 112 (which may be composed of multiple independently controllable linkages or a single, unitary member) and portable support base 102, to position and/or orient the magnetic stator system 10 in a desired location relative to the patient. The positioning assembly 112 may include multiple pivots, joints, and/or hydraulic mechanisms that each can be adjusted individually or in combination. The positioning assembly 112 can adjust the magnet pod 110 along multiple axes or without restriction (e.g., six degrees of freedom) in order to provide precise positioning with respect to a patient. For example, the magnet pod 110 may be configured to rotate about two or more axes of rotation. The positioning assembly 112 may include locking mechanisms to prevent movement once a desired orientation and position is obtained. In some embodiments, the magnetic control system 10 can be positioned perpendicular to the patient's body (e.g., head, arm, or leg) at a distance of between 2 and 20 cm (e.g., between 2 and 6 cm, between 4 and 10 cm, between 6 and 12 cm, between 8 and 20 cm, overlapping ranges thereof, 8 cm, or any distance within the recited ranges) from the patient's body. The magnetic control system 10 can be configured to be substantially secured in place during use or it can be configured to move during use through manual operation, automatic operation, or some combination thereof.

In some embodiments, a rotating magnetic field is generated by mechanically rotating a strong permanent magnet having an orientation that rotates the field at a target site, and at the same time presents a steady magnetic gradient in a desired direction. Rotational frequencies (e.g., greater than or equal to 0.1 Hz and/or less than or equal to 100 Hz, including but not limited to from about 1 Hz to about 30 Hz, from about 3 Hz to about 10 Hz, from about 0.5 Hz to about 50 Hz, from about 1 Hz to about 6 Hz, from about 0.1 Hz to about 10 Hz, from about 5 Hz to about 20 Hz, from about 10 Hz to about 30 Hz, from about 20 Hz to about 50 Hz, from about 40 Hz to about 70 Hz, from about 50 Hz to about 100 Hz, overlapping ranges thereof, less than 5 Hz, less than 10 Hz, less than 20 Hz, less than 30 Hz, less than 40 Hz, less than 50 Hz) can be effective with a range of magnetic field magnitudes that can be generated by magnets (e.g., greater than or equal to 0.01 Tesla and/or less than 1 Tesla, including but not limited to from about 0.01 Tesla to about 0.1 Tesla, from about 0.05 Tesla to about 0.5 Tesla, from about 0.1 Tesla to about 0.6 Tesla, from about 0.3 Tesla to about 0.9 Tesla, from about 0.5 Tesla to about 1 Tesla, overlapping ranges thereof, less than 1 Tesla, less than 0.5 Tesla, less than 0.25 Tesla, less than 0.1 Tesla). Gradient strength can be greater than or equal to 0.01 Tesla/m and/or less than or equal to 10 Tesla/m, including but not limited to from about 0.01 Tesla/m to about 1 Tesla/m, from about 0.01 Tesla/m to about 3 Tesla/m, from about 0.05 Tesla/m to about 5 Tesla/m, from about 1 Tesla/m to about 4 Tesla/m, overlapping ranges thereof, less than 5 Tesla/m, less than 3 Tesla/m, less than 2 Tesla/m, less than 1 Tesla/m). The gradient direction generally centers on the center of mass for a permanent magnet. Polarity of the magnets may also be switched to control agglomeration and/or movement of the magnetic particles.

The system may further include a medical instrument (e.g., catheter, microcatheter, infusion catheter, infusion wire) configured to administer or deliver the magnetic particles within the patient. In some embodiments, magnetic particles (e.g., nanoparticles) are locally administered to a location near (e.g., proximate, adjacent) a therapeutic target or fluid obstruction through a catheter (e.g., a microcatheter). The medical instrument may be configured to inject the magnetic particles transcutaneously or transdermally through needle-guided access based on visualization using the diagnostic and/or imaging system. For example, computed tomography angiography or diagnostic ultrasound imaging systems and modalities can be used to identify a location of a therapeutic target (e.g., clot or area of occlusion, such as chronic total occlusion or a tumor). In some embodiments, a catheter is introduced intra-arterially and advanced to a location adjacent a clot within neurovasculature, a cerebral artery, a coronary artery, any peripheral artery or any other artery. In some embodiments, a catheter is introduced intravenously and advanced to a location adjacent an obstruction within one or more veins (e.g., veins of a limb such as an arm or leg). A catheter or other delivery device could be introduced to provide epidural delivery, lymphatic delivery, trans-ureteral delivery, or other mechanism of delivery of magnetic particles and/or therapeutic or theranostic agents.

In some embodiments, the magnetic particles themselves function as contrast agents that can be imaged or detected by an imaging modality without requiring delivery of a separate contrast media or agent to facilitate imaging. For example, the magnetic particles (e.g., monocrystalline or polycrystalline iron oxide nanoparticles) themselves may constitute contrast agents based on the makeup of the nanoparticles and can be opaque to certain imaging modalities or technologies. In various embodiments, the nanoparticles may comprise at least one of gadolinium, manganese, copper, nickel, cobalt, zinc, germanium, gold, silver, compounds comprising group II (A or B) and group VI elements, compounds comprising group IV and group VI elements, bioluminescence agents, combinations thereof, and the like. In some embodiments, the magnetic particles comprise theranostic structures, in that they provide both diagnostic and therapeutic capabilities. For example, the magnetic particles may include a therapeutic agent conjugated or coated or otherwise attached to the magnetic particles. Imaging of the magnetic particles can inform the clinician as to duration of time of exposure to the therapeutic agent, whether the therapeutic agent is administered separately or is a component of some or all of the magnetic particles.

In accordance with several embodiments, contrast media, bioluminescence or other materials may be attached to (e.g., conjugated to or adsorbed to) or doped into the magnetic particles (e.g., nanoparticles, microparticles) for chemical, magnetic, therapeutic, diagnostic, theranostic and/or imaging reasons. Example contrast coatings include contrast coatings detectable by X-ray, PET, MR and ultrasound imaging technologies.

In some embodiments, contrast media (e.g., diagnostic or theranostic agents) may be delivered together with the magnetic particles or separately from the magnetic particles to facilitate or enhance imaging (for example, if the magnetic particles themselves cannot be effectively imaged). The contrast media may be delivered through the same medical instrument and in the same manner as the magnetic particles or may be delivered separately (e.g., through systemic intravenous infusion or intra-arterial infusion through a separate catheter or other medical instrument). The contrast media and/or magnetic particles may be delivered to or through any body lumen, channel, space, volume or passage, including vasculature, Fallopian tubes, cerebrospinal spaces or passages, gastrointestinal tract (e.g., intestines, colon), ureters, lymphatic system (lymph nodes), intraosseous locations (e.g., bone cavities or spaces), liver, lungs, heart, pericardium, peritoneum, thoracic cavity, brain, etc. In some embodiments, the diagnostic agents (e.g., contrast media) are not attached to the particles but simply mixed with or co-administered with the particles.

The diagnostic or imaging modalities or technologies may include X-ray, ultrasound, radiography, magnetic resonance, nuclear medicine, photo acoustic, thermography, tomography (PET, CT), fluoroscopy, magnetic localization, and/or any other modalities or technologies. The imaging technologies and systems can be used to transmit images to a display device to provide an operator real-time feedback so that the operator can navigate or otherwise control movement of the magnetic particles (e.g., nanoparticles) and so that the operator can be informed regarding subsequent treatment of the therapeutic target.

The magnetic control systems and magnetic nanoparticles may be used in conjunction with any diagnostic or imaging scan, such as but not limited to angiograms, arteriograms, venograms, PET scans, CT scans, X-rays, elastography scans, lymphography scans, thermograms, sonograms, encephalograms, and/or the like. In certain implementations, control of the magnetic field by the magnetic control system may be integrated with control of the imaging modality (e.g., interlaced) by the imaging system to minimize interference between the systems and optimize performance (e.g., image display, magnetic field control, prevent aliasing due to overlapping or interfering frequency ranges).

As an example, a real-time user interface on a display can incorporate image information from a diagnostic or imaging system. The imaging system can be a system incorporating one or more imaging modalities, configured to provide imaging data to the magnetic control system. The imaging data can be derived from x-ray data, PET data, MR data, CT scan data, ultrasonic imaging data, or other imaging modality data, as described herein.

The operator may receive or view imaging data from the imaging system (e.g., on a display monitor communicatively coupled to the imaging system). In some embodiments, the imaging data comprises information derived from an imaging modality that, in use, provides information about the therapeutic target and/or about the magnetic particles, which can inform subsequent treatment of the therapeutic target by a clinician medical professional. For example, the imaging system can produce image data based on ultrasound-based imaging. The imaging system can transmit sound waves aimed at an area of interest and interpret the echoed waves to produce an image. The ultrasound-based imaging system can be configured to provide imaging data in real-time and can be configured to identify fluid flow, tissue, liquid, magnetic particles, and the like. In some embodiments, the information about the therapeutic target can include information about the morphology (e.g., shape) and structure (e.g., size, rigidity) and type of therapeutic target.

Identifying the magnetic particles can include analyzing the imaging data for signals associated with magnetic nanoparticles. For example, in ultrasonic imaging, the magnetic particles can have a distinctive signal in an image due to their motion, composition, position, behavior, orientation, or any combination of these. As another example, in PET systems, the magnetic particles can have a distinctive and/or identifiable signal in an image based on attached contrast agents, the density or composition of the particles, the position of the particles, or the like.

Some embodiments of the invention relate to the control of magnetic particles (e.g., nanoparticles) to increase contact of a therapeutic target (e.g., clot, thrombus, occlusion, obstruction) in a portion of a circulatory system (e.g., artery, vein) with a therapeutic agent (e.g., a pharmaceutical compound, a thrombolytic drug, microplasmin, plasmin or naturally-occurring thrombolytic within the body such as plasminogen, neuroprotectant, anti-inflammatory agent, cardioprotectant), which can result in increased fluid flow and the substantial clearance of fluid blockages, or obstructions, of body lumens (e.g., vasculature, blood vessels, organs, tubes, canals) or of temporary or permanent in-dwelling devices inserted within the body (e.g., shunts, tubes, drainage conduits, ports, stents, catheters, implants with lumens).

In various aspects, the systems and methods described herein advantageously enhance diffusion of one or more therapeutic, diagnostic or combined therapeutic and diagnostic (theranostic) agents or delivery of the therapeutic, diagnostic or theranostic agents to a region of low or no flow. Magnetic fields and gradients can be used to act on magnetic nanoparticle agglomerates (e.g., stir bars or stir rods) to travel to desired treatment or diagnostic locations and/or to reduce obstructions or blockages, including vascular occlusions, in a patient. In various aspects, the system and methods described herein can be used to treat fluid blockages of the circulatory system in the head (in particular, the brain) and vessels within and surrounding the heart and in the extremities of the body, such as the vasculature (e.g., arteries, veins) of limbs (e.g., arms and legs).

In various aspects, the system and methods described herein can be used simply to transport therapeutic agents (e.g., as a "payload") through or along body passages that are difficult to access or traverse in an invasive or minimally invasive approach or to keep the therapeutic, diagnostic or theranostic agents in place for an extended period of time before they are washed downstream due to ordinary fluid flow. In some implementations, tissue plasminogen activator and one or more of plasminogen, microplasmin and plasmin are delivered to a clot to facilitate enhanced lysis efficacy. In other implementations, pro-coagulant materials (e.g., thrombin) and/or fibrinogen may be delivered using the magnetic particles so as to create clots at targeted, isolated locations so as to prevent internal bleeding at the locations. The magnetic particles may be coated or packaged together with the pro-coagulant materials. The pro-coagulant materials may act on the fibrinogen (e.g., delivered separately after localization of the pro-coagulant materials by control of the rotating magnetic field) to create the clots.

The magnetic control systems and magnetic nanoparticles described herein may also be used to facilitate identification, and clearing, of obstructions within in-dwelling devices (e.g., catheters, shunts, infusion or injection ports, stents, drainage tubes, drainage lines or conduits, or other implants). If obstructions in in-dwelling devices are not cleared out, they may be ineffective in reducing swelling or alleviating other symptoms. The embodiments described herein may advantageously allow for clearing of obstructions within in-dwelling devices without having to perform invasive surgery and/or without requiring removal or replacement of the devices. For example, contrast media may be delivered in conjunction with magnetic nanoparticles to facilitate imaging of flow within the in-dwelling devices to determine the location of the obstructions or blockages within the devices and then to facilitate clearing of the obstructions or blockages without having to remove and/or replace the devices.

Magnetically-Responsive Flow Generator

FIGS. 4A-4E schematically illustrate an embodiment of a magnetically-responsive flow generator 400 and operation thereof. The magnetically-responsive flow generator 400 may be used to facilitate clearance of one or more obstructions or blockages in a blood vessel, other bodily lumen, or an in-dwelling device. The magnetically-responsive flow generator 400 may be advanced through a catheter (e.g., guide catheter, microcatheter) in conjunction with other devices or methods (e.g., thrombectomy devices, therapeutic, diagnostic, or theranostic agent delivery, neurovasculature or peripheral vasculature treatment or diagnostic procedures). The magnetically-responsive flow generator 400 comprises an elongate wire or shaft 405 having a proximal end portion 406 and a distal end portion 407. The proximal end portion 406 of the elongate wire 405 may extend out of a body of a subject and may be manipulated (manually by a hand of a clinician or automatically (e.g., using a robotic system)) to advance and retract the elongate wire 405 with respect to an outer catheter or sheath 408 (e.g., guide catheter, microcatheter). The proximal end portion 406 may be operably coupled to a handle and/or catheter port to facilitate manipulation (e.g., advancement and retraction and optionally rotation). The elongate wire 405 may be sufficiently flexible to navigate a tortuous path of multiple curves or bends. The elongate wire or shaft 405 may be formed of a material that is not magnetic or responsive to a magnetic field (e.g., a non-ferrous metal such as copper or aluminum, or a polymer material that is biocompatible). In other embodiments, the elongate wire or shaft 405 may comprise ferrous or magnetic material. In some embodiments, the elongate wire or shaft 405 may include a lumen and can be advanced over a guidewire. In some embodiments, the elongate wire or shaft 405 does not include a lumen. A rotor 410 (e.g., pinwheel, propeller) may be rotatably coupled to the distal end portion 407 of the elongate wire 405 to allow the rotor 410 to freely and continuously rotate, or spin, about a central longitudinal axis of the elongate wire 405. The rotor 410 may be adapted to rotate, or spin, in a clockwise and/or counter-clockwise direction. The rotor 410 may include a central rotating hub and a plurality of outwardly-extending, or radiating, blades or arms coupled thereto. The blades or arms may be evenly spaced about the hub. The blades or arms may be angled to facilitate generation of flow, similar to an airplane or boat propeller. The rotatable coupling may comprise a roto hinge or a swivel connector mechanism or assembly, for example, such that the rotor 410 rotates independently of the elongate wire 405. In other words, the elongate wire 405 remains fixed while the rotor 410 rotates in response to a rotating magnetic field.

In alternative configurations, the rotor 410 may be adapted to rotate simultaneously with the elongate wire 405. Thus, rotation of the elongate wire 405 causes rotation of the rotor 410.

As shown, the rotor 410 may comprise multiple blades, fins, arms, or other extensions 411 shaped and adapted to generate fluid flow (e.g., cause fluidic currents or vortexes) adjacent to an obstruction or blockage within a body lumen (e.g., blood vessel, passage, channel) or catheter or implant (e.g., shunt, drainage tube, line). The flow may be generated even in regions of no flow, stagnant flow, or low flow. The rotor 410 (or at least the multiple blades, fins, arms, or other extensions 411) may be formed of magnetically-responsive material such that generation of a rotating magnetic field by an external magnetic control system 10 (e.g., incorporating one or more permanent magnets or electromagnets) causes rotation of the rotor 410 with respect to the elongate wire 405. For permanent magnet implementations, the external magnetic control system 10 may include one and only one permanent magnet or multiple permanent magnets positioned at various locations that operate in combination or in succession, such as shown schematically in FIG. 4E). The rotor 410 may be formed of shape memory material (e.g., nickel-titanium alloy, copper-aluminum-nickel alloy, or other metallic and/or polymeric alloy) such that the rotor 410 may be advanced through the outer catheter or sheath 408 (e.g., guide catheter) in a compressed configuration and then may automatically spring or flex outward to an expanded, default configuration upon removal of the constraint of the outer catheter 408.

Figure 4A:
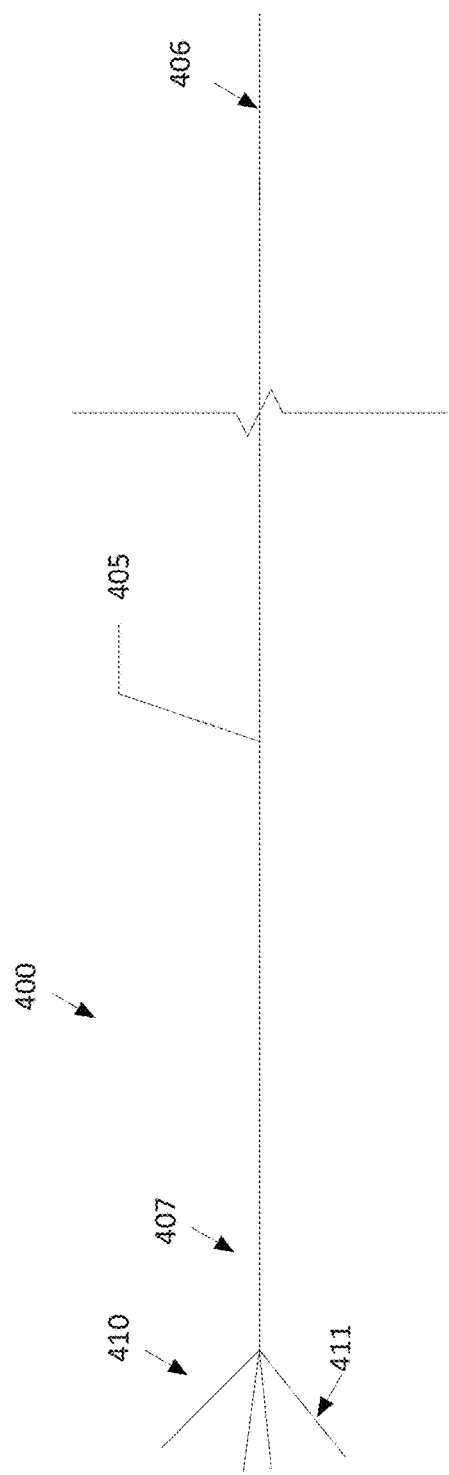
Figure 4B:
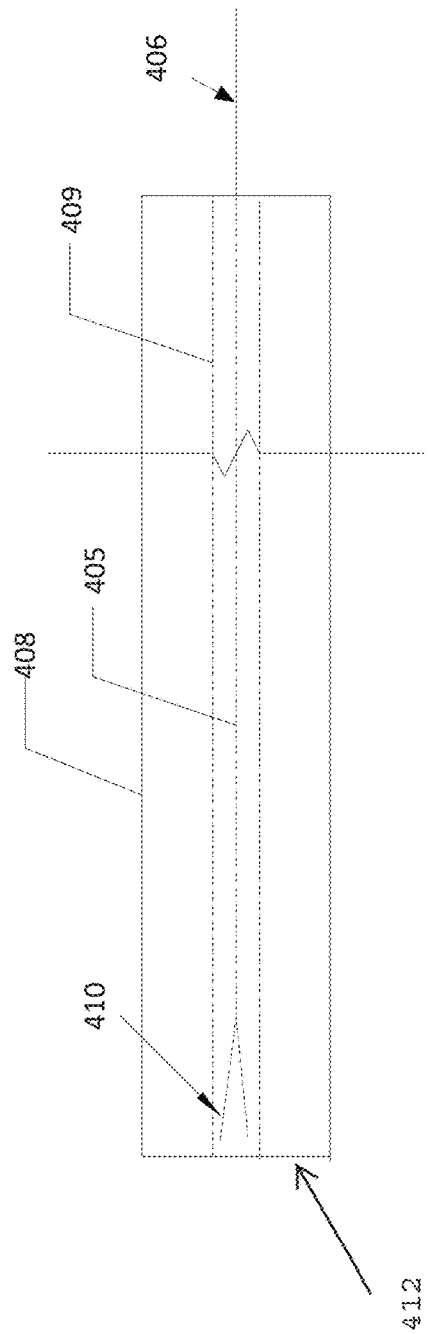

With reference to FIG. 4B, the rotor 410 may be advanced in a compressed configuration along a lumen 409 of an outer catheter 408 (e.g., guide catheter) to a distal end of the outer catheter 408. With reference to FIG. 4C, as the rotor 410 is advanced out of an opening 412 at the distal tip of the outer catheter 408, the blades 411 of the rotor 410 begin to flex outward toward a default, expanded configuration. In FIG. 4D, the blades of the rotor 410 have been fully flexed to the default, expanded configuration. FIG. 4D also includes a front or top view of the rotor 410 when in a fully expanded configuration. In some embodiments, the blades 411 of the rotor 410 lie at a 90-degree angle with respect to a central longitudinal axis of the elongate wire 405 or the outer catheter 408. In some embodiments, the blades 411 of the rotor 410 may rest at an angle less than 90 degrees (e.g., between 60 and 90 degrees, between 75 and 90 degrees, between 80 and 90 degrees, overlapping ranges thereof, or any value within the recited ranges). The blades or other extensions 411 may all have a uniform length or may have different lengths. The blades or other extensions 411 may each be equally spaced apart from each other or may have other groupings and spacings as desired and/or required. The number of blades or other extensions 411 may be two, three, four, five, six, seven, eight, or more than eight, as desired and/or required. The blades or other extensions 411 may not comprise any sharpened surfaces.

In other implementations, one or more surfaces of the blades or other extensions 411 may be abrasive and/or sharpened to facilitate mechanical break-up of a blockage or obstruction.

Figure 4E:
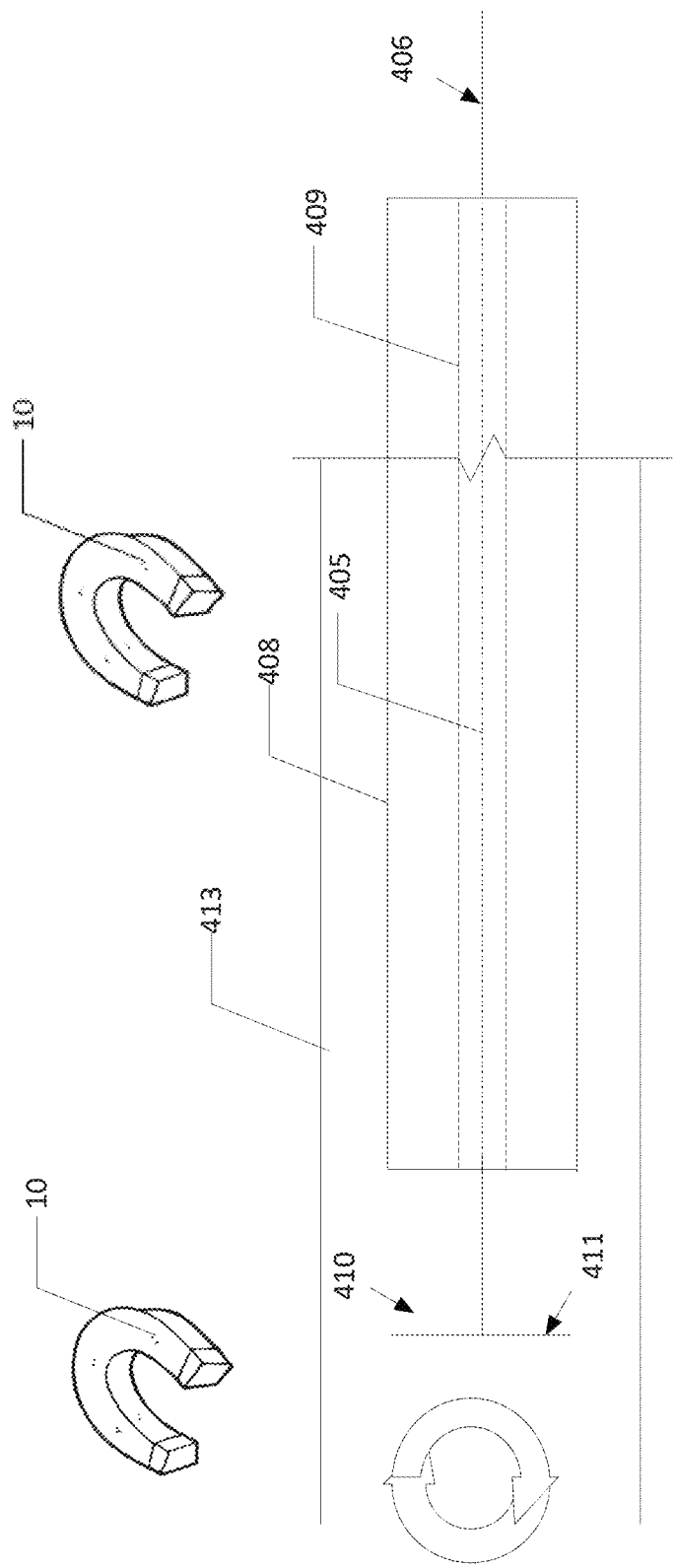

With reference to FIG. 4E, the external magnetic control system 10 may be activated to generate a rotating magnetic field to cause rotation of the rotor 410 to generate flow within a body lumen 413 or within a lumen of an in-dwelling device. The flow may cause a therapeutic agent previously or concurrently delivered through the outer catheter 408 or through a separate instrument to flow toward an obstruction, blockage, or occlusion (e.g., a clot within neurovasculature, a thrombus, a region of stenosis, a chronic total occlusion). After a desired period of rotation, the external magnetic control system 10 may be deactivated and the rotor 410 may be pulled back into the outer catheter 408 by pulling proximally on the elongate wire 405. Therapeutic agents may comprise a structure (e.g., composition) configured to deliver a payload to a therapeutic or diagnostic target (e.g., cancerous tissue, a site of infection, a diagnostic imaging target). The payload could include an anti-inflammatory agent.

The magnetic control system 10 can include any magnetic control system (such as those described herein in connection with FIG. 3 or in WIPO Publ. No. 2013/173235 and previously incorporated herein by reference) that facilitates control of orientation, position, rotation of a magnet or magnetic field. For permanent magnet implementations, the external magnetic control system 10 may include one and only one permanent magnet or multiple permanent magnets positioned at various locations that operate in combination or in succession, such as shown schematically in FIG. 4E. The polarity of the one or more magnets may be adjusted to control manipulation of individual magnetic particles or agglomerated magnetic particles.

In accordance with several embodiments, the magnetically-responsive flow generator 400 advantageously provides a solution for generating fluid flow that does not require an active mechanism (e.g., motor) coupled to the elongate wire or rotor to cause rotation and that does not require significant real estate (e.g., cross-sectional area) within a lumen of the outer catheter (e.g., guide catheter). In various embodiments, the magnetically-responsive flow generator 400 requires less than one-fourth (e.g., less than 25%), less than one-third (less than 33%), less than one-fifth (less than 20%), between 5% and 40%, of a total cross-sectional area of the outer catheter 408.

In alternative embodiments, the rotor 410 may comprise a paddle wheel, a stirrer, a whisk, or other flow-generation mechanism. In some configurations, the blades or other extensions 411 are replaced by a continuous body that includes cut-outs, slits, or different curves or profiles formed on various portions of the continuous body (e.g., around a circumference of the continuous body) adapted to facilitate fluid flow or generate fluidic currents. The fluid flow generated may comprise circular fluid motions, vortexing fluid motions, shear fluid motion, propagating wave fluid motion, and/or other fluid motion.

In some embodiments, one or more therapeutic agents or theranostic agents may be delivered through the outer catheter 408 (either through the same lumen as the magnetically-responsive flow generator 400 or a different lumen). The one or more therapeutic agents or theranostic agents may be conveyed to a therapeutic target (e.g., blockage or obstruction) by the fluidic currents or fluid flow generated by the magnetically-responsive flow generator 400. Therapeutic agents or theranostic agents may comprise a structure (e.g., composition) configured to deliver a payload to a therapeutic or diagnostic target (e.g., cancerous tissue, a site of infection, a diagnostic imaging target). The payload could include an anti-inflammatory agent. In some embodiments, the magnetically-responsive flow generator 400 may be hidden inside a delivery sheath or hidden inside a lumen of the outer catheter 408 and may be un-sheathed by retracting the delivery sheath or outer catheter 408 or by pushing the magnetically-responsive flow generator 400 out of the delivery sheath or lumen (e.g., via a pusher, such as a shaft, wire or tube).

In some embodiments, the magnetically responsive flow generator 400 may be configured to remain inside a lumen of the outer catheter 408 and not advance out of the distal end of the outer catheter 408. Instead, the rotor 410 may comprise multiple blades (e.g., 3 or 4 blades) that remain in the lumen of the outer catheter and create flow similar to a ceiling fan such that when the rotor 410 is actuated in a first rotational direction, the rotor 410 spins and the blades generally create a "pushing" flow in a first translational direction away from the blades and when the rotor 410 is actuated in a second rotational direction opposite the first rotational direction, the blades generally create a "pulling" or "siphoning" flow toward the blades in a second translational direction.

Obstruction Removal from In-Dwelling Devices

As discussed above, stents, shunts, lines, tubes, catheters, ports, and/or other infusion, injection, or drainage devices are sometimes temporarily or permanently inserted or implanted within a body of a patient. The devices can become blocked or obstructed over time (e.g., due to tissue ingrowth or due to the body's immune response to a foreign object). It can be expensive, annoying, dangerous, time-consuming, and/or invasive to remove the temporary or permanent in-dwelling device for cleaning or to replace the in-dwelling device with a new replacement device.

In accordance with several embodiments, magnetic particles (e.g., magnetic nanoparticles or microparticles) may be organized to form stir bars or stir rods as described herein using external magnetic control systems (e.g., control system 10) to advantageously facilitate removal of obstructions or blockages within these in-dwelling devices while the devices remain inserted within the body. The stir bars or stir rods may either generate fluid flow that in and of itself clears the obstruction or blockage or the stir bars or stir rods may carry or convey therapeutic or mechanical agents adapted to break down (e.g., lyse, scour through abrasion, dissolve, etc.) the obstructions or blockages to the location(s) of the obstruction(s) or blockage(s). The removal of the obstructions or blockages may advantageously allow for continued operation and function of the in-dwelling devices. The continued operation and function of the in-dwelling device may reduce swelling, for example, that, if left unaddressed, could cause permanent damage in neurovascular applications (such as shunt or tube for drainage of cerebrospinal fluid). The magnetic particles may either be introduced after insertion of the in-dwelling device (e.g., shunt or tube) or may be embedded within the in-dwelling devices prior to insertion of the in-dwelling device. The magnetic particles may include therapeutic agents adapted to facilitate removal, lysis, breakdown of obstructions within the in-dwelling devices and/or body lumens surrounding the in-dwelling devices. The therapeutic agents may be attached or unattached to the magnetic particles. In some embodiments, the magnetic particles do not include therapeutic agents.

The in-dwelling devices may include, for example, PICC lines, temporary catheters, injection or infusion ports, chest tubes, thoracostomy tubes, feeding tube, drainage tube, surgical drains, ostomy tube, nephrostomy tube, port-a-caths for chemical infusion or injection, brain shunts to drain cerebrospinal fluid, arteriovenous shunts, cardiovascular shunts, intestinal bypass shunts, peritoncovenous shunts, mesocaval shunts, portacaval shunts, portosystemic shunts, pulmonary shunts, splenorenal shunts, ventriculoatrial shunts, ventriculoperitoneal shunts, ventriculovenous shunts, endoluminal stents, endovascular stents, urologic stents, bypass grafts, stent-grafts, aneurysm coil, glaucoma drainage devices, lymphatic drainage devices, wound drainage devices, and/or the like.

Figure 5A:
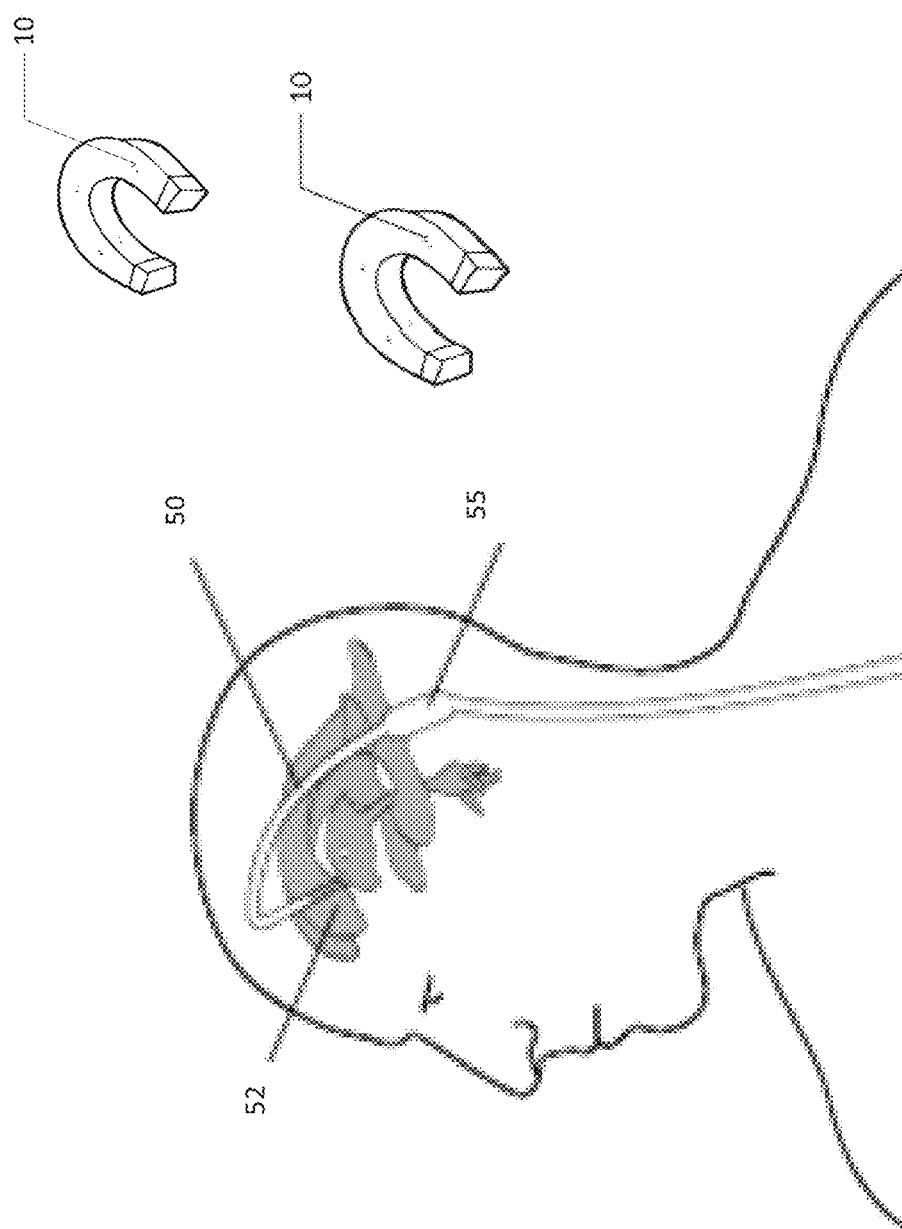
FIGS. 5A and 5B schematically illustrate a method of clearing shunts or lines used as drains or conduits within a subject using magnetically-controlled magnetic particles.
Figure 5B:
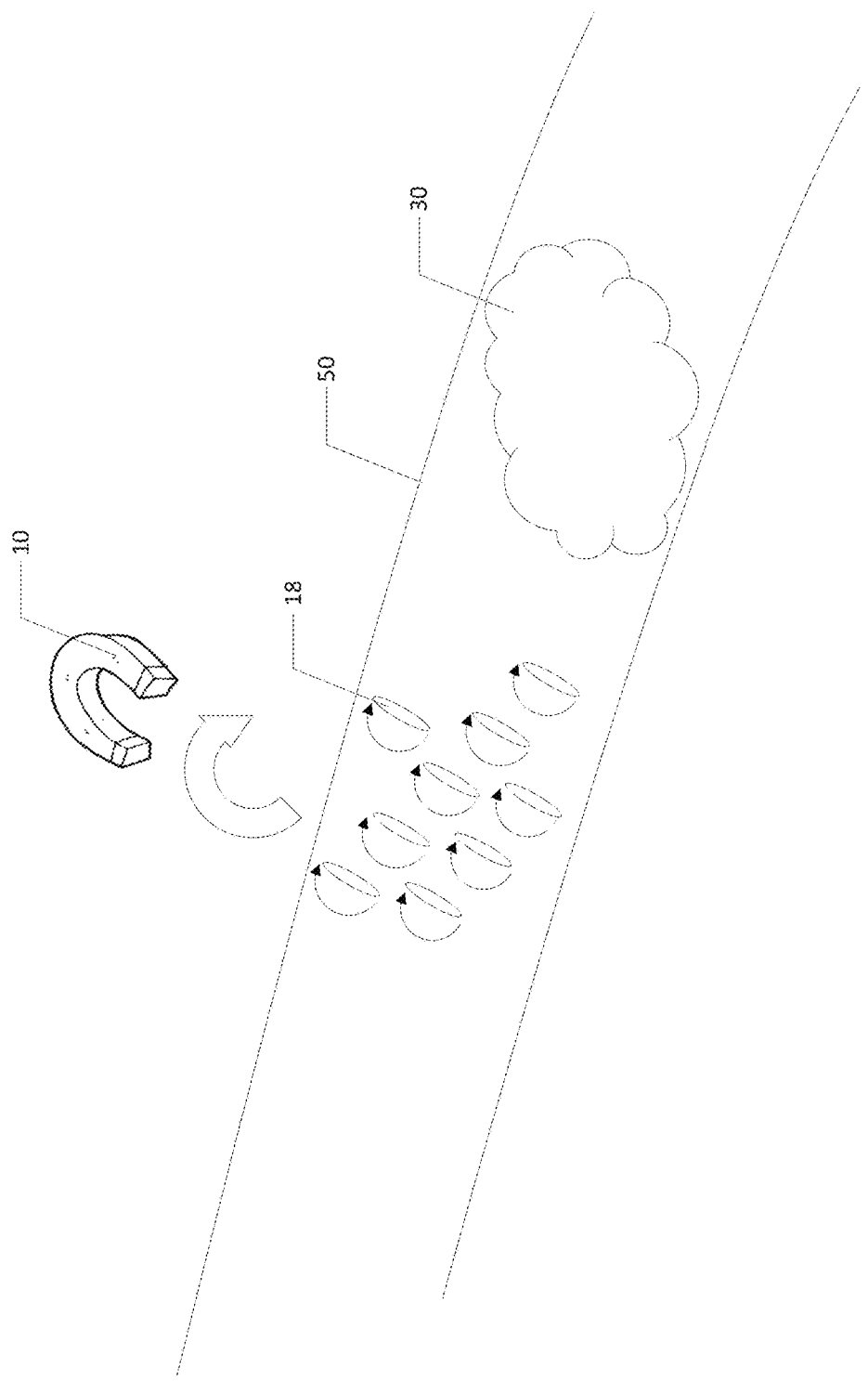

FIGS. 5A and 5B illustrate an example of how the magnetic particle and magnetic controller technology described herein and described in Applicant's applications previously incorporated by reference may be used to remove obstructions within a brain shunt 50, which is an example of an in-dwelling device. The brain shunt 50 may include a valve 55. Magnetic particles (e.g., magnetic nanoparticles) may be delivered through a delivery catheter to a location adjacent the brain shunt 50. The magnetic particles may delivered to a location adjacent either a proximal or distal end of the brain shunt 50. For example, for a brain shunt 50 extending from a location within the brain (e.g., within one or more ventricles 52 of the brain) to a drainage location within a peritoneal cavity or other drainage location, the magnetic particles may be conveyed either to the brain (e.g., ventricles 52) or to the peritoneal cavity of other drainage location. In some embodiments, the delivery catheter is inserted via an incision in a femoral artery, a brachial artery, a radial artery, a carotid artery, or other artery. An external magnetic control system 10 is then activated to generate a rotating magnetic field to cause the particles to agglomerate into stir bars or stir rods 18 and travel toward and within the brain shunt 50. For permanent magnet implementations, the external magnetic control system 10 may include one and only one permanent magnet or multiple permanent magnets positioned at various locations that operate in combination or in succession, such as shown schematically in FIG. 5A.

With reference to FIG. 5B, the rotation of the stir bars or stir rods 18 generates fluidic currents that cause the breakdown of any obstructions or blockages 30 within any portion of the brain shunt 50, thereby increasing flow through the brain shunt 50 and advantageously reducing swelling in the brain without having to remove or replace the brain shunt 50. In some embodiments, one or more therapeutic agents adapted to break down (e.g., dissolve, lyse) the obstructions or blockages 30 may also be delivered through the delivery catheter. The generated fluidic currents may facilitate conveyance of the one or more therapeutic agents (e.g., lytic fluid agent) to the obstructions or blockages 30. There may be multiple obstructions or blockages 30 even though only one is illustrated. In some embodiments, the particles may be coated or otherwise comprise the therapeutic agents instead of delivering them separately. The stir bars 18 may be imaged (using one or more imaging modalities) so as to identify a location of any obstructions or blockages 30. For example, the particles may comprise a contrast agent or theranostic agent capable of being imaged. The particles may include features to facilitate imaging by one or more modalities, such as described in Applicant's published applications previously incorporated by reference.

In other embodiments, the in-dwelling device (e.g., brain shunt 50 or other shunt or indwelling tube) may include embedded magnetic particles that are included in the in-dwelling device with the initial delivery of the in-dwelling device to a desired location within a subject. These embedded magnetic particles may remain within the in-dwelling device and may be activated by the external magnetic control system periodically as desired and/or required to clear the in-dwelling device (e.g., brain shunt 50 or other shunt or tube). The magnetic particles may include therapeutic agents adapted to facilitate removal, lysis, breakdown of obstructions within the in-dwelling devices and/or body lumens surrounding the in-dwelling devices. The therapeutic agents may be attached or unattached to the magnetic particles. In some embodiments, the magnetic particles do not include therapeutic agents.

Additional Language and Conclusion

In some embodiments, the systems comprise various features that are present as single features (as opposed to multiple features). For example, the systems may consist of a single permanent magnet as opposed to multiple magnets. In other embodiments, multiple features may be used (such as multiple magnets working together instead of a single magnet). In some embodiments, the systems comprise one or more of the following: means for controlling rotation of a magnet, means for delivering magnetic particles (e.g., intravenous or intra-arterial infusion assembly or intravascular catheter), etc.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. The headings used herein are merely provided to enhance readability and are not intended to limit the scope of the embodiments disclosed in a particular section to the features or elements disclosed in that section.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter" include "instructing advancing a catheter." The ranges disclosed herein also encompass any and all overlap, sub-ranges, and combinations thereof. Language such as "up to," "at least," "greater than," "less than," "between." and the like includes the number recited. Numbers preceded by a term such as "about" or "approximately" include the recited numbers. For example, "about 1000 nm" includes "1000 nm." Terms or phrases preceded by a term such as "substantially" or "generally" include the recited term or phrase. For example, "substantially continuously" includes "continuously."

What is claimed is:

1. A method of facilitating treatment of a therapeutic target within a body of a subject, the method comprising:
    delivering a magnetically-responsive flow generator to a location adjacent the therapeutic target, the magnetically-responsive flow generator comprising:
        an elongate wire having a proximal end and a distal end, wherein the elongate wire does not comprise magnetically-responsive material; and
        a rotor rotatably coupled to the proximal end of the elongate wire, the rotor comprising magnetically-responsive material, wherein the rotor is configured to rotate about a central longitudinal axis of the elongate wire while the elongate wire remains stationary; and
    applying a rotating magnetic field from outside the body of the subject so as to cause the rotor to rotate, wherein rotation of the rotor generates fluid flow toward the therapeutic target.

2. The method of claim 1, wherein delivering the magnetically-responsive flow generator to the location adjacent the therapeutic target comprises inserting the magnetically-responsive flow generator into a lumen of a catheter and advancing the magnetically-responsive flow generator along the lumen of the catheter until the rotor of the magnetically-responsive flow generator exits the lumen of the catheter.

3. The method of claim 1, wherein applying the rotating magnetic field comprises causing rotation of at least one permanent magnet of an external magnetic control system.

4. The method of claim 1, wherein applying the rotating magnetic field comprises generating a rotating magnetic field with an electromagnet.

5. The method of claim 1, wherein the rotor comprises a propeller with a plurality of blades.

6. The method of claim 5, wherein the blades do not comprise any sharpened surfaces.

7. The method of claim 1, wherein the therapeutic target is a clot within a blood vessel, an obstruction within an in-dwelling device, an obstruction within a body lumen, a chronic total occlusion within a blood vessel, a stenotic lesion within a blood vessel, or a region of low fluid flow.

8. The method of claim 1, wherein the rotor comprises shape memory material configured to expand into a default expanded configuration when unconstrained.

9. A magnetically-responsive flow generator configured to generate flow at a location adjacent a therapeutic target within a subject, the magnetically-responsive flow generator comprising:
    an elongate wire having a proximal end and a distal end, wherein the elongate wire does not comprise magnetically-responsive material; and
    a rotor rotatably coupled to the proximal end of the elongate wire, the rotor comprising magnetically-responsive material,
    wherein the rotor is configured to rotate about a central longitudinal axis of the elongate wire in response to application of a rotating magnetic field while the elongate wire remains stationary.

10. The magnetically-responsive flow generator of claim 9, wherein the rotor comprises shape memory material.

11. The magnetically-responsive flow generator of claim 9, wherein the rotor is configured to self-expand into a default, expanded configuration when unconstrained.

12. The magnetically-responsive flow generator of claim 9, wherein the rotor comprises multiple outwardly-extending members sized and shaped to generate flow upon rotation of the rotor.

13. The magnetically-responsive flow generator of claim 12, wherein the outwardly-extending members comprise propeller blades.

14. The magnetically-responsive flow generator of claim 13, wherein the rotor comprises four propeller blades.

* * * * *